(12) United States Patent
Trovato et al.

(10) Patent No.: US 12,397,114 B2
(45) Date of Patent: *Aug. 26, 2025

(54) COMPOUNDING DEVICE SYSTEM

(71) Applicant: Omnicell, Inc., Mountain View, CA (US)

(72) Inventors: Giuseppe Trovato, Trieste (IT); Andrea Schiavinato, Trieste (IT); Luca Amato, Bolzano (IT); Charles Marsh, Cranberry Township, PA (US); Larry McCutchan, Allison Park, PA (US)

(73) Assignee: Omnicell, Inc., Cranberry Township, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/734,678

(22) Filed: Jun. 5, 2024

(65) Prior Publication Data

US 2024/0316267 A1     Sep. 26, 2024

Related U.S. Application Data

(60) Division of application No. 18/168,616, filed on Feb. 14, 2023, now Pat. No. 12,042,632, which is a
(Continued)

(30) Foreign Application Priority Data

Nov. 23, 2017   (IT) .................... 102017000134813

(51) Int. Cl.
| | | |
|---|---|---|
| *H04N 23/56* | (2023.01) | |
| *A61M 5/178* | (2006.01) | |
| *G01G 19/52* | (2006.01) | |
| *G01G 21/22* | (2006.01) | |
| *G16H 20/10* | (2018.01) | |
| *G16H 20/17* | (2018.01) | |

(Continued)

(52) U.S. Cl.
CPC .......... *A61M 5/1782* (2013.01); *G01G 19/52* (2013.01); *G01G 21/22* (2013.01); *G16H 20/10* (2018.01); *G16H 20/17* (2018.01); *H04N 23/56* (2023.01); *H04N 23/57* (2023.01); *H04N 23/90* (2023.01); *A61M 2005/3125* (2013.01); *A61M 2205/3313* (2013.01); *A61M 2205/3393* (2013.01); *G01G 17/00* (2013.01)

(58) Field of Classification Search
CPC ........ A61M 5/1782; A61M 2005/3125; A61M 2205/3313; A61M 2205/3393; H04N 23/56; H04N 23/57; H04N 23/90; G16H 20/17; G16H 20/10; G01G 19/52; G01G 21/22; G01G 17/00
USPC .......................................... 705/3, 2; 348/159
See application file for complete search history.

(56) References Cited

U.S. PATENT DOCUMENTS 9,959,628 B2 *   5/2018  Mutti ........................ G06T 7/13

\* cited by examiner

*Primary Examiner* — Trang U Tran
(74) *Attorney, Agent, or Firm* — Kilpatrick Townsend & Stockton LLP; Darin J. Gibby; Torrey D. Spink

(57) ABSTRACT

A system for compounding medications. The system includes one or more compounding devices, and a central computer system. The central computer system receives requests, at least some of which require the compounding of one or more medications, and pushes assignments of respective compounding tasks to the one or more compounding devices. The assignments are made in accordance with a set of rules designed to promote efficient use of compounding resources.

18 Claims, 14 Drawing Sheets

Related U.S. Application Data division of application No. 17/209,625, filed on Mar. 23, 2021, now Pat. No. 11,590,283, which is a continuation of application No. 16/792,519, filed on Feb. 17, 2020, now Pat. No. 10,967,125, which is a continuation of application No. 16/207,016, filed on Nov. 30, 2018, now Pat. No. 10,596,319, which is a continuation-in-part of application No. 15/865,038, filed on Jan. 8, 2018, now Pat. No. 10,991,264.

(60) Provisional application No. 62/592,609, filed on Nov. 30, 2017.

(51) Int. Cl.
*H04N 23/57* (2023.01)
*H04N 23/90* (2023.01)
*A61M 5/31* (2006.01)
*G01G 17/00* (2006.01)

COMPOUNDING DEVICE SYSTEM

CROSS REFERENCE TO RELATED APPLICATIONS

This application is a divisional of U.S. patent application Ser. No. 18/168,616, filed Feb. 14, 2023 and titled "Compounding Device System," which is a divisional of U.S. patent application Ser. No. 17/209,625, filed Mar. 23, 2021 and titled "Compounding Device System," which is a continuation of U.S. patent application Ser. No. 16/792,519, filed Feb. 17, 2020 and titled "Compounding Device System," which is a continuation of U.S. patent application Ser. No. 16/207,016, filed Nov. 30, 2018 and titled "Compounding Device System," which is a continuation-in-part of U.S. patent application Ser. No. 15/865,038, filed Jan. 8, 2018 and titled "Multi-Camera Imaging for IV Compounding," which claims priority to Italian patent application no. 102017000134813 filed Nov. 23, 2017, and U.S. patent application Ser. No. 16/207,016, filed Nov. 30, 2018 and titled "Compounding Device System" claims the benefit of Provisional U.S. Patent Application No. 62/592,609 filed Nov. 30, 2017 and titled "Compounding Device System," the entire disclosures of which are hereby incorporated by reference herein for all purposes.

BACKGROUND OF THE INVENTION

Pharmaceutical compounding is the preparation of patient-specific medications by the processing or combination of ingredients. Many medications, especially medications administered orally in pill form, are now manufactured in a variety of forms and dosages so that little preparation is needed at a pharmacy, other than placing the proper number of pills in a bottle to fill a doctor's prescription for a particular patient. However, medications for intravenous delivery are routinely compounded, for example in hospital pharmacies.

Typically, a physician will prescribe a particular medication or a combination of medications for a specific patient, for intravenous (IV) delivery. The pharmacy receives the prescription and prepares the IV solution with the proper amount of each prescribed medication. The compounded medication is then sent to the hospital floor for administration to the patient.

It is of utmost importance that the correct medications be prepared in the correct proportions, without the introduction of contaminants. Detailed protocols may be developed for the compounder to follow. The number of different protocols may be very large, because there may be a large number of different medications to choose from, in a variety of packages, to be prepared in a number of dosages, and to be provided in a number of different delivery vehicles.

Much of the work of compounding may be delegated to workers who are not registered pharmacists, or to robotic machines. Accordingly meticulous records may be kept of the preparation of each medication, so that the pharmacist can review how each medication was made before it leaves the pharmacy. The records also enable review of the preparation of any particular medication at a later time, should there be any question of its correctness.

In addition, it is desirable that pharmacy resources be used efficiently, and that excessive waste of medications and supplies be avoided.

BRIEF SUMMARY OF THE INVENTION

A system for compounding of medications comprises one or more compounding devices, and a computer. Each of the one or more compounding devices is in bidirectional communication with the computer via an electronic network. The computer is configured to receive a plurality of requests, at least some of which require the compounding of one or more medications, and for each of the received requests, push, via the electronic network, an assignment of a respective compounding task to one of the one or more compounding devices. The computer is configured to assign respective compounding tasks in accordance with a set of rules designed to promote efficient use of compounding resources.

DETAILED DESCRIPTION OF THE INVENTION

Figure 1:
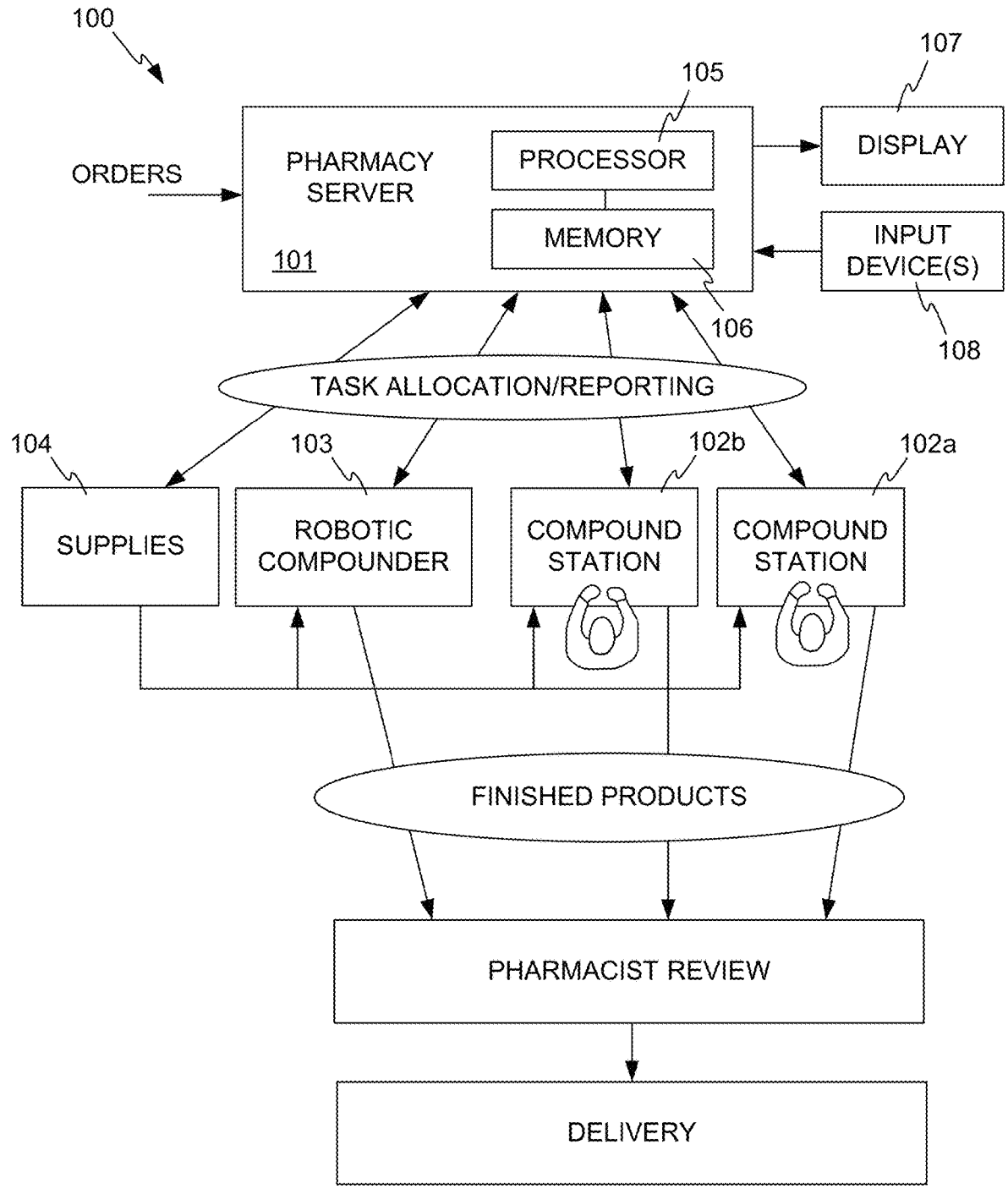
FIG. 1 illustrates a compounding pharmacy in accordance with embodiments of the invention.

FIG. 1 illustrates a compounding pharmacy 100 in accordance with embodiments of the invention. The operation of pharmacy 100 is coordinated by a pharmacy server 101, described in more detail below. Pharmacy server 101 receives orders for compounded medications, for example prescriptions from physicians. Pharmacy server 101 maintains extensive records of orders received, detailed protocols for the compounding of medications, records of the preparation of medications in response to orders, and other items. Pharmacy server 101 also allocates tasks to one or more compounding stations, which may include manual compounding stations such as stations 102a and 102b, and one or more robotic compounders 103. The compounding stations may also report information to pharmacy server 101, for example records of the compounding of each ordered medication.

Pharmacy server 101 includes a processor 105 and memory 106. Memory 106 holds instructions that, when executed by processor 105, cause pharmacy server 101 to perform its functions in accordance with embodiments of the invention. Memory 106 may also hold the records, protocols, and other information collected and generated in the operation of pharmacy 100. For the purposes of this disclosure, the term "memory" encompasses many different kinds of data storage devices and combinations of such devices, for example dynamic memory, static memory, volatile memory, nonvolatile memory, and mass storage such as magnetic or optical disk storage or tape storage.

While pharmacy server 101 is shown as a single block in FIG. 1 and could be a single, stand-alone computer system having memory 106 and one or more processors 105, other implementations are possible. For example, pharmacy server 101 may be implemented using a number of interconnected computers, either co-located or in multiple locations. In particular, pharmacy server 101 may be implemented as a "cloud" service, in which the functions of pharmacy server 101 may be performed by different processors at different times, and memory 106 may be distributed as well. Pharmacy server 101 presents information to a user via a user interface shown on an electronic display 107, and may receive inputs from the user via any input device or devices 108, for example a keyboard, mouse, other pointing device, or other input devices or combinations of input devices.

Working materials are supplied to the compounding stations from a supply store 104. Pharmacy server 101 may maintain an inventory of the materials in supply store 104, and may track the movements of medications and supplies within pharmacy 100.

Finished products are reviewed by the pharmacist and delivered from pharmacy 100 to their points of use, for example patient rooms for administration by a nurse to a patient. It will be understood that the above description is highly generalized, and that a working compounding pharmacy may have many other systems and facilities.

Figure 2:
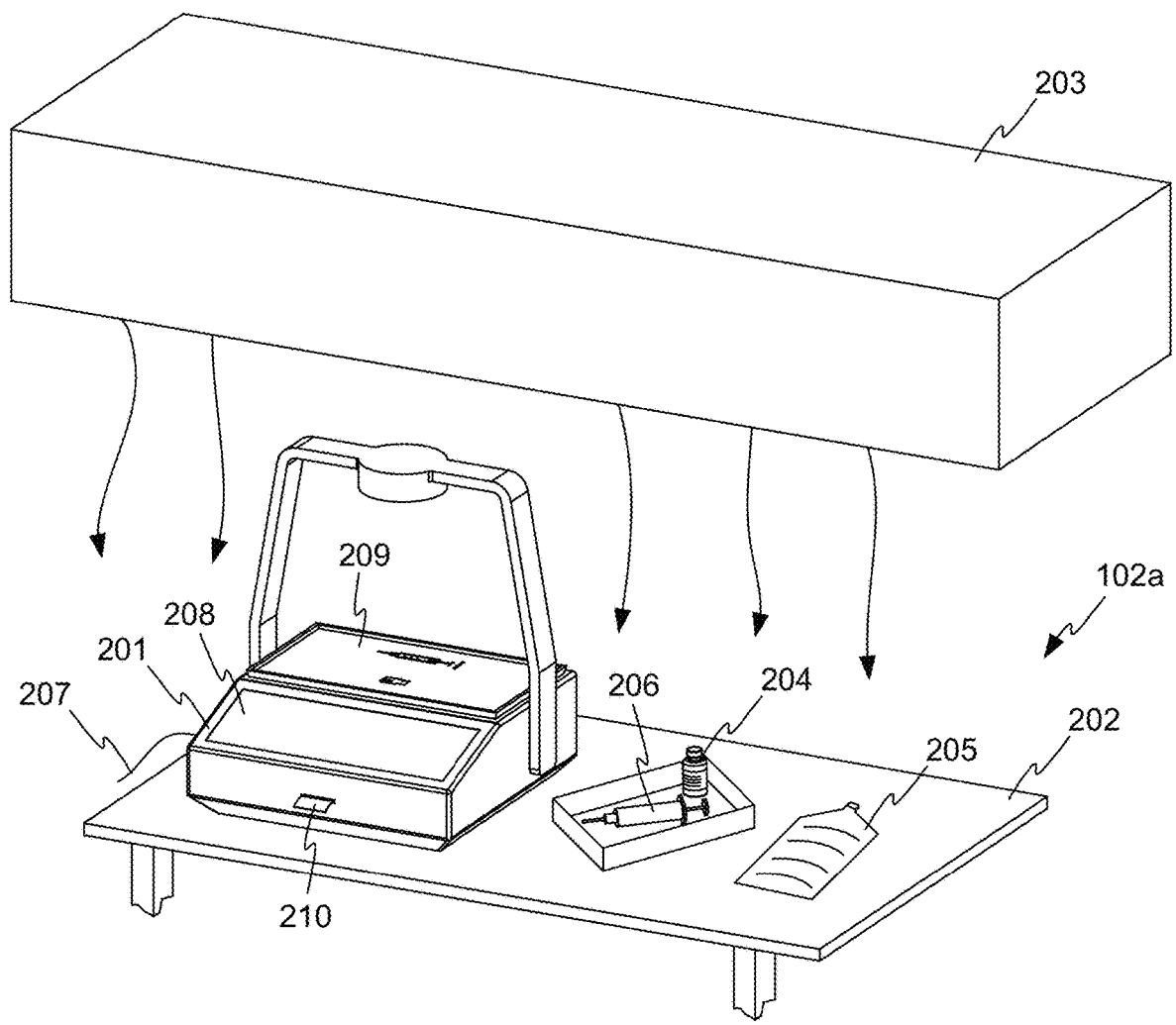
FIG. 2 illustrates a manual compounding station in accordance with embodiments of the invention.

FIG. 2 illustrates a manual compounding station 102a in accordance with embodiments of the invention. Compounding station 102a includes a compounding assistance device 201 on a surface 202. For the purposes of this disclosure, a compounding assistance device is an electromechanical device having features and capabilities for facilitating the performance of a compounding task by a human operator. Compounding assistance device 201 may be placed under a laminar flow hood 203, which flows filtered air over compounding assistance device 201 and surface 202, to help avoid contamination of the materials being worked on, and for protection of the user of compounding station 102a.

In the example shown, compounding station 102a has received supplies for a simple compounding task. A medication supplied in a vial 204 is to be added to an IV drip bag 205. A syringe 206 may be used to accomplish the transfer.

Compounding assistance device 201 has several features and capabilities that will assist the compounder in properly preparing the formulation in IV drip bag 205, and in thoroughly documenting the process. Compounding assistance device 201 has a network connection 207 to pharmacy server 101, through which compounding assistance device 201 may receive a protocol from pharmacy server 101 describing the steps required to perform the compounding task.

For the purposes of this disclosure, a protocol is a sequence of steps for a specific compounding task involving a specific medication. A workflow is a generic set of steps, specified independent of the particular medication and dosage of the specific compounding task. One workflow can describe the generic steps required for a kind of compounding task. Many different protocols may implement the workflow, for specific medications and amounts. For example, a particular workflow may describe the high level steps needed to draw medication from a vial and add it to an IV drip bag. Separate protocols can then describe the steps for placing a specific dosage of a specific medication in the drip bag.

Compounding assistance device 201 includes a display screen 208 on which instructions to the user may be presented or through which the user may input information. For example, display screen 208 may be a touchscreen display, sensitive to touch and able to distinguish the location of a touch. Compounding assistance device 201 also includes a tray 209 which provides a carrier for holding items while they are weighed or photographed, as is described in more detail below.

Figure 3:
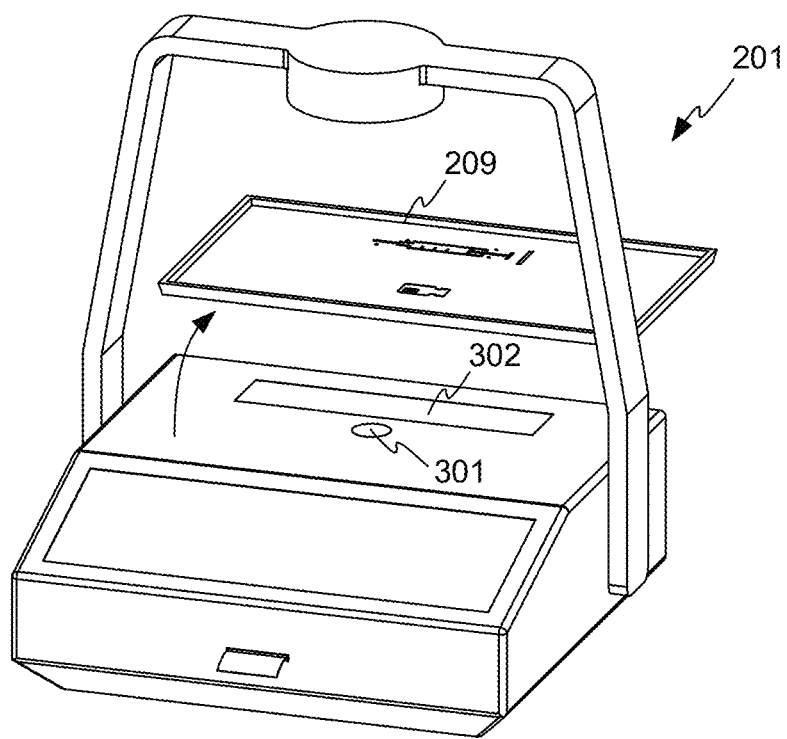
FIG. 3 shows a compounding assistance device, in accordance with embodiments of the invention.

FIG. 3 shows compounding assistance device 201, with tray 209 removed, in accordance with embodiments of the invention. Visible in FIG. 3 is a weight sensor 301, for example a load cell, for weighing tray 209 and its contents. Also visible is an area light source 302. Area light source 302 is a two-dimensional extended or area light source, and emits light from many points or continuously across its face. Area light source 302 may be, for example, an infrared light panel, illuminating a portion of tray 209 from below with infrared light.

Figure 4:
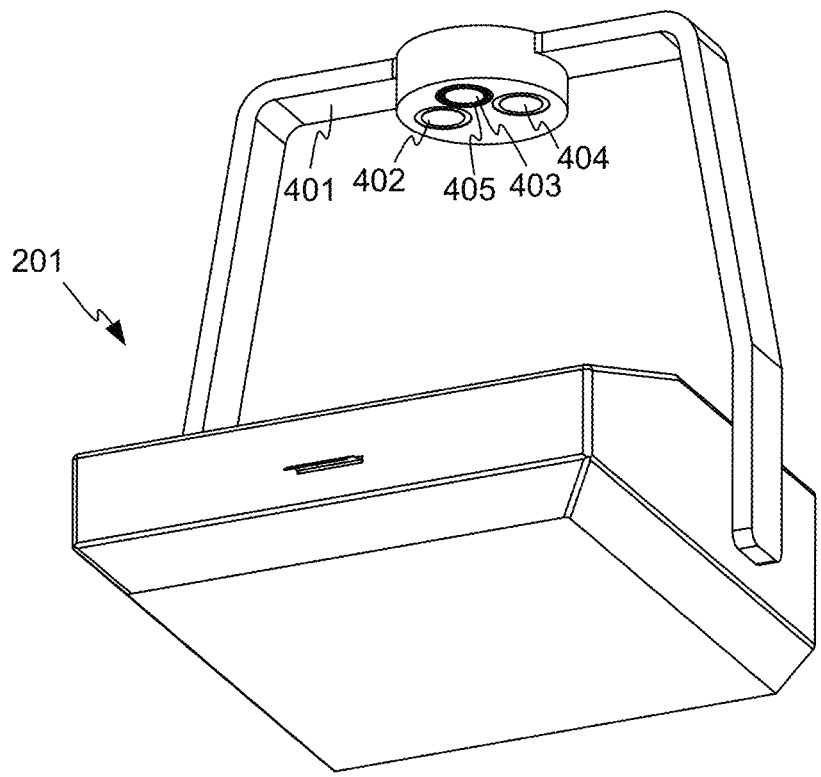
FIG. 4 shows a lower oblique view of the compounding assistance device of FIG. 3, in accordance with embodiments of the invention.

FIG. 4 shows a lower oblique view of compounding assistance device 201, in accordance with embodiments of the invention. A gantry 401 spans tray 209. Positioned on gantry 401 are a bar code scanner 402, a visible light camera 403, and an infrared camera 404. Visible light camera 403 may further include one or more light sources 405 for illuminating at least a portion of tray 209 from above. Light sources 405 may be, for example, one or more white-light light emitting diodes (LEDs) surrounding visible light camera 403, or another kind of light source. For the purposes of this disclosure, light is "visible" if it includes light wavelengths between about 400 and 700 nanometers. Light is "white" if it includes enough wavelengths in the visible range to enable reasonably complete color recognition.

The area above tray 209 may be called a viewing area for items to be photographed by infrared camera 404 or visible light camera 403, or scanned by bar code scanner 402. In other embodiments, an item may not necessarily be lit from below and photographed from above. For example, in a compounding robot, a robotic mechanism may hold an item to be photographed in the field of view of a camera in any orientation. For example, an item may be photographed from below, or horizontally.

Bar code scanner 402 is positioned to read bar codes on items held in the viewing area between tray 209 and bar code scanner 402. Visible light camera 403 and infrared camera 404 are position to take photographs of items on tray 209.

During compounding of a medication one or more of weight sensor 301, bar code scanner 402, visible light camera 403, and infrared camera 404 can be used to provide documentation of how the medication was compounded, and to avoid errors.

For example, to perform the compounding task illustrated in FIG. 2, pharmacy server 101 sends detailed sequential instructions to compounding assistance device 201, which then leads the user through the steps required to formulate the specific medication in the specific dose required, for delivery in the specific delivery vehicle. In this example, the task may involve transferring 30000 units of Heparin (a common anticoagulant) from a vial containing 5000 units/ml of Heparin in solution, to an IV drip bag. The volume of solution required for transfer is therefore 6 ml. Vial 204 and IV drip bag 205 have been supplied to compounding station 102a, along with syringe 206, which will be needed to make the transfer.

Figure 5:
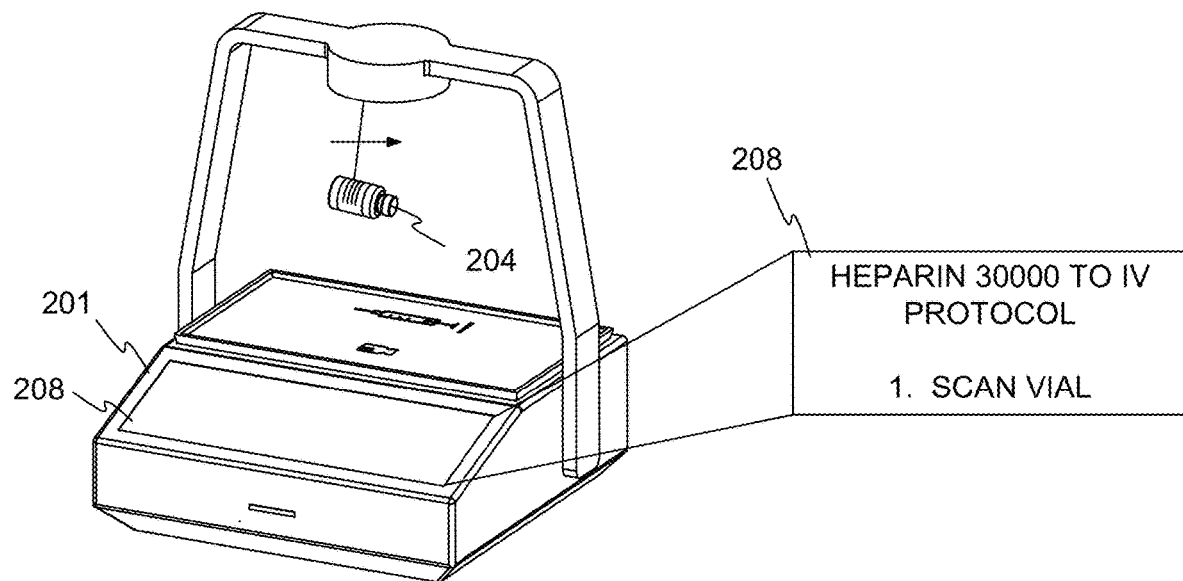
FIG. 5 illustrates bar code scanning by the compounding assistance device of FIG. 3, in accordance with embodiments of the invention.

First, compounding assistance device 201 requires that the user present vial 204 to bar code scanner 402, so that the identifying bar code on vial 204 can be read, and the system can verify that the correct vial with the correct concentration has been provided. If not, then an error message is generated and the compounding task is stopped. The scanning process is illustrated in FIG. 5, along with an example prompt shown on screen 208. Compounding assistance device 201 may automatically recognize that the barcode has been detected, and may move to the next step. Alternatively, an acknowledgment from the user may be required, in this and other steps.

Figure 6:
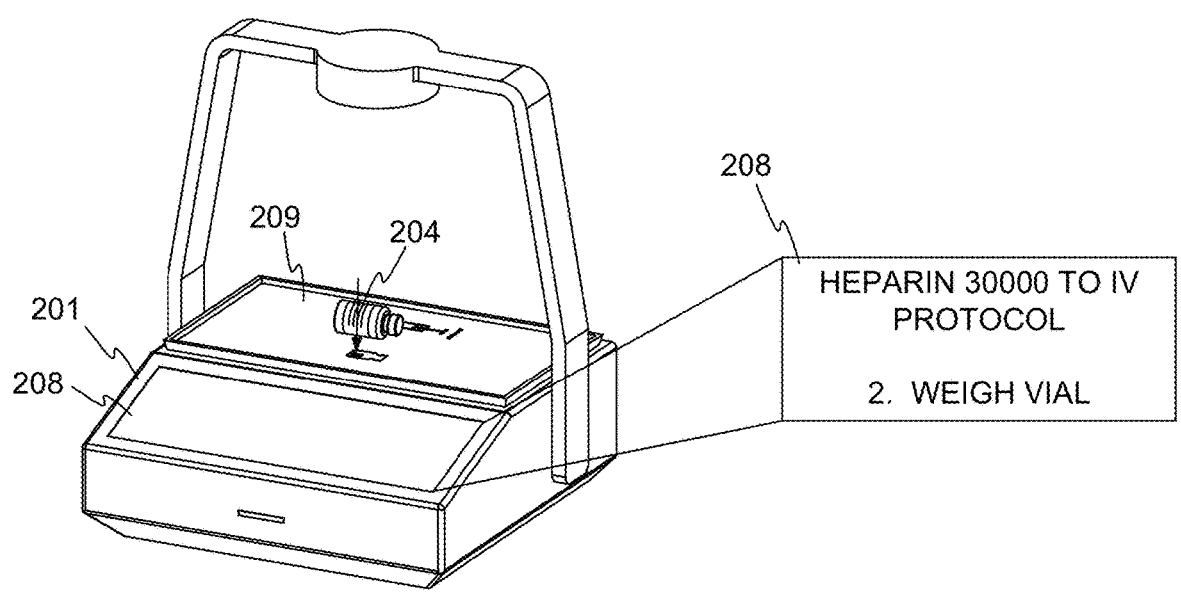
FIG. 6 illustrates a step in a compounding process, in accordance with embodiments of the invention.

FIG. 6 illustrates a second step in the compounding process, in which an initial weight of vial 204 is collected. For this purpose, vial 204 is placed on tray 209. Tray 209 may include an icon 601 indicating where vial 204 should be placed, and may also include mechanical features for aiding in proper placement of vial 204. For example, a gently V-shaped trough may be formed into tray 209. Compounding assistance device 201 may automatically recognize the weight of vial 204 on tray 209, record the weight, and move to then next step of the compounding process.

In some embodiments, vial 204 may also be photographed while on tray 209 using visible light camera 403, using ambient light, light from light sources 405, or a combination thereof.

Figure 7:
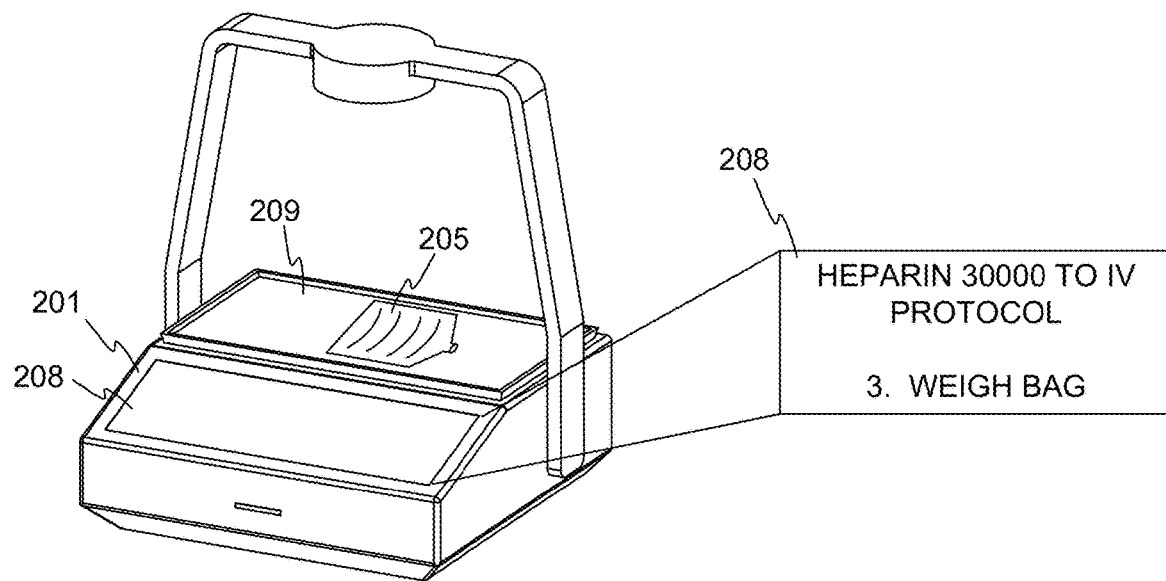
FIG. 7 illustrates another step in the compounding process, in accordance with embodiments of the invention.

FIG. 7 illustrates a third step, in which an initial weight of IV bag 205 is collected. Compounding assistance device 201 may then prompt the user to draw the correct amount (6 ml) of solution from vial 204 into syringe 206.

Figure 8:
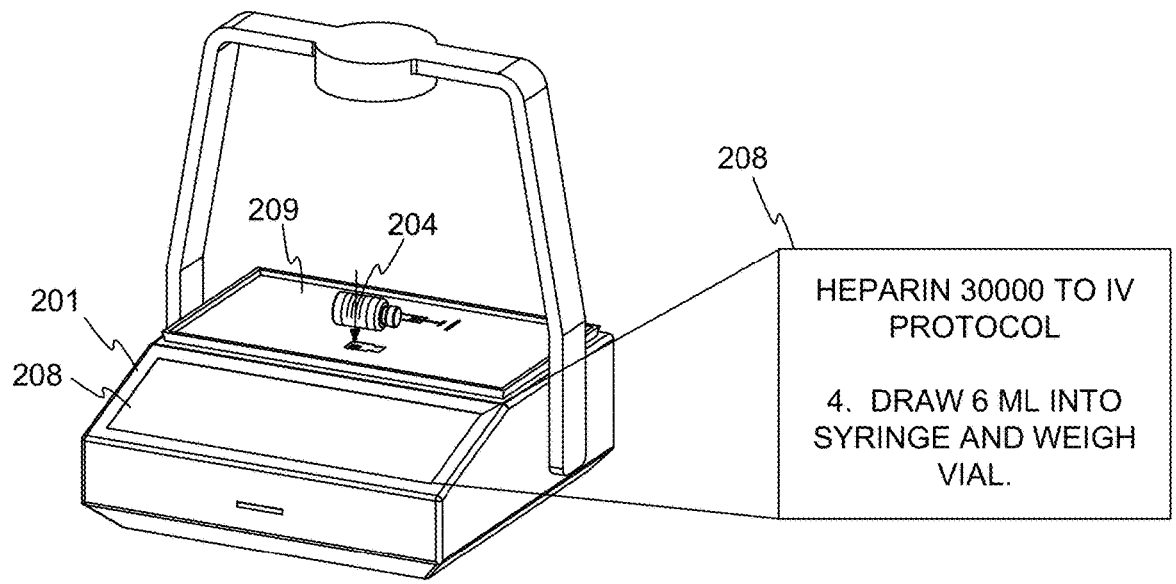
FIG. 8 illustrates another step in the compounding process, in accordance with embodiments of the invention.

FIG. 8 illustrates a fourth step, in which an after-drawn weight of vial 204 is taken, in a manner similar to the taking of the initial vial weight shown in FIG. 6. The system can compare the two weights of vial 204 to calculate the amount of solution drawn from vial 204, for recordkeeping and for verification that the proper amount of solution was drawn.

Figure 9:
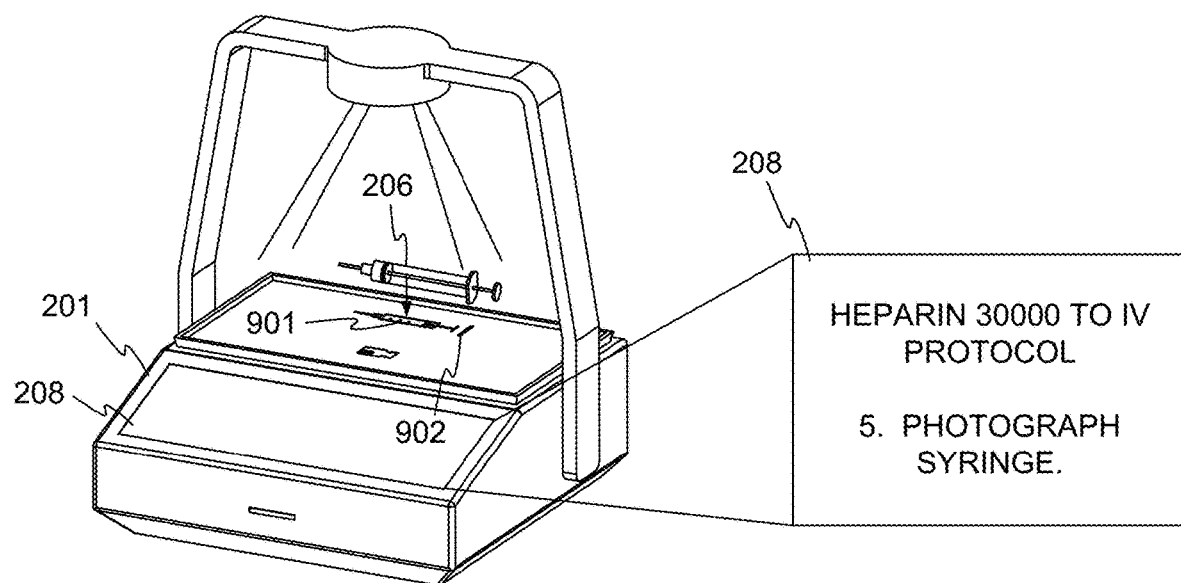
FIG. 9 illustrates another step in the compounding process, in accordance with embodiments of the invention.

FIG. 9 illustrates a fifth step, in which the filled syringe is photographed. For this purpose, tray 209 may include an icon 901 for placement of syringe 206, and may include mechanical features facilitating correct placement and alignment of syringe 206 on tray 209, for example a V-shaped trough, or a groove 902 shaped and sized to receive an edge of the barrel flange of syringe 206. Other fiducial marks may be present as well.

Figure 10:
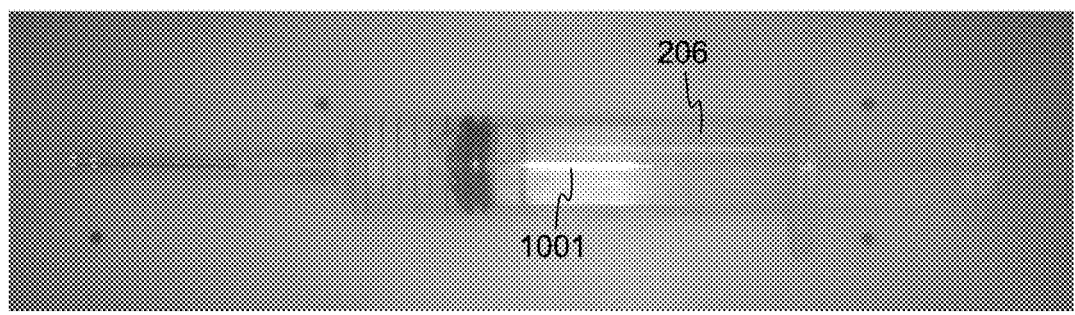
FIG. 10 shows a photograph as may be taken using a visible light camera, in accordance with embodiments of the invention.

Syringe 206 may be photographed using visible light camera 403, but is preferably photographed using infrared camera 404. FIG. 10 shows a photograph as may be taken using visible light camera 403. (Visible light camera 403 preferably has a field of view larger than shown in FIG. 10, but syringe 206 has been isolated from the larger view for ease of explanation.) While syringe 206 is readily visible in the photograph of FIG. 10, the photograph has been affected by glare spot 1001, and may have been affected by ambient light sources that are not under the control of compounding assistance device 201.

Figure 11:
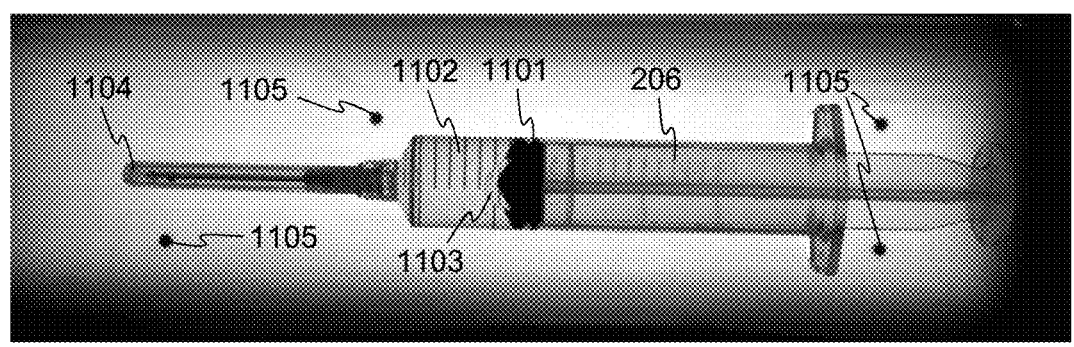
FIG. 11 shows a photograph of a syringe as may be taken using an infrared camera, in accordance with embodiments of the invention.

FIG. 11 shows a photograph of syringe 206 as may be taken using infrared camera 404. Tray 209 is not opaque to infrared radiation, so syringe 206 is backlit by infrared light source 302. For example, tray 209 may be substantially transparent to infrared radiation, or may be translucent. In some embodiments, tray 209 may be made of polycarbonate or another suitable polymer or blend of polymers. Infrared camera 404 may have a wavelength-selective optical filter that passes infrared light to camera 404, but blocks the visible spectrum. Thus, glare spots formed from visible light are excluded from the photograph of FIG. 11, resulting in greater clarity of features of syringe 206.

Whichever kind of camera is used, compounding assistance device 201 can automatically analyze the resulting photograph for any of a number of purposes. For example (referring to FIG. 11), the position of the plunger 1101 of syringe 206 may be automatically recognized, and the amount of drawn liquid 1102 calculated based on the known dimensions of syringe 206. In some embodiments, bubbles such as bubble 1103 may be detected and flagged if they are large enough to significantly affect the dose of medication being prepared. In some protocols, the weight of syringe 206 before and after drawing liquid from vial 204 may be used to verify that the correct amount of liquid was placed into syringe 206. In that case, compounding assistance device 201 may also photograph syringe 206 at each weighing and analyze the photographs to detect whether syringe cap 1104 may have been mistakenly included in one weighing but not another. Fiducial marks 1105 on tray 209 are placed in known positions, and may be detected in the photograph and used to calibrate distances in the photograph.

Figure 12:
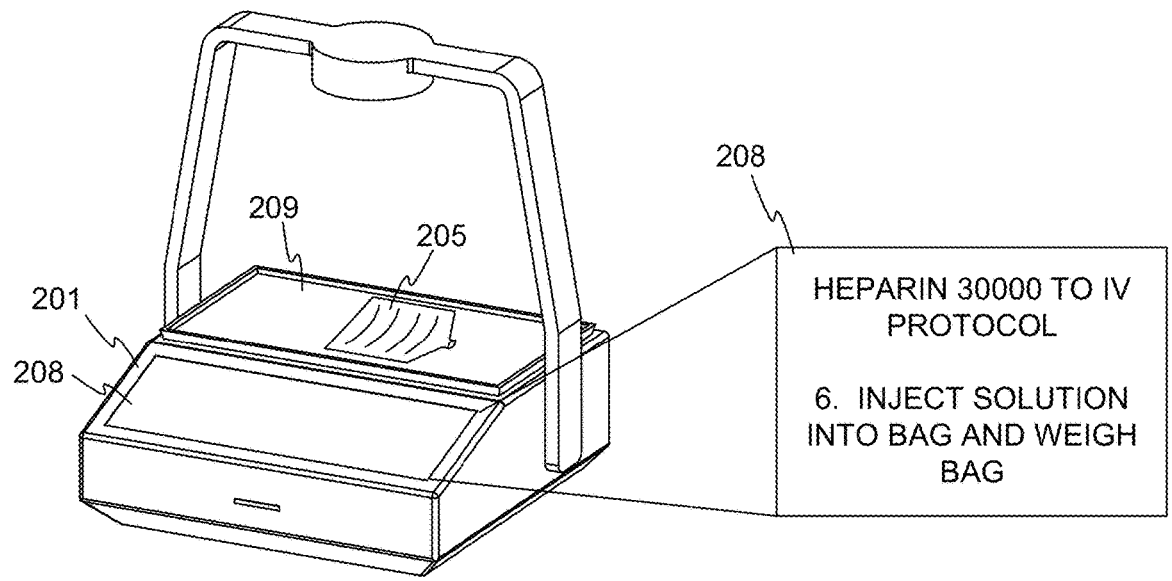
FIG. 12 illustrates another step in the compounding process, in accordance with embodiments of the invention.

FIG. 12 illustrates a sixth step, in which IV bag 205 is re-weighed after addition of solution from syringe 206. Compounding assistance device 201 can compare the before and after weights of bag 205 to verify that the correct amount of Heparin solution was placed into bag 205.

Figure 13:
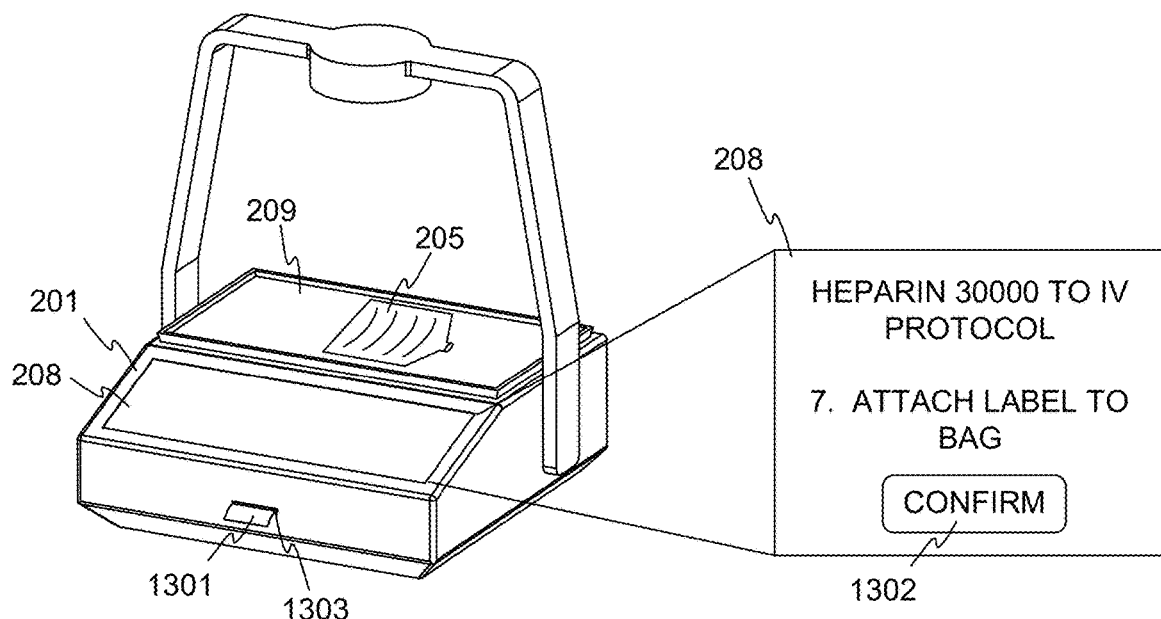
FIG. 13 illustrates another step in the compounding process, in accordance with embodiments of the invention.

FIG. 13 illustrates a seventh step, in which (presuming all of the checks in the system have verified that the compounding process was done correctly) compounding assistance device 201 prints a label 1301 using label printer 1303, to be placed on bag 205, and the user is prompted to adhere label 1301 to bag 205. The finished medication can then be delivered to its point of use, and any consumable items disposed of, for example syringe 206. The user may be asked to confirm 1302 that label 1301 has been affixed, using display 208. In some embodiments, a final photograph of completed bag 205 may be taken for pharmacist review.

The compounding process described above is but one example, and many different compounding workflows may be implemented that have different steps, that use different medication containers, that collect different or additional information for process verification, or that differ in other ways from the example shown.

While the above example was shown in the context of compounding workstation 102a, a similar process may be followed for compounding using a robotic compounder such as robotic compounder 103 shown in FIG. 1. A robotic compounder is a machine, usually enclosed, that use a robotic mechanism to handle vials, syringes, bags, and the like to prepare compounded medications. A robotic compounder may include a scale, one or more cameras, agitation devices, disposal ports, material and supply loading windows, and a delivery window for delivering a finished medication. Robotic compounders are not subject to human error in the compounding process, but include various weight and photographic checks on their work to guard against improper loading of materials, mechanical malfunctions, programming errors, and the like.

Whether compounding is done manually or robotically, the data collected during the compounding process is stored, for example on pharmacy server 101, and can be reviewed by the responsible pharmacist. For example, the pharmacist can verify that the correct kind of vial containing the correct medication was identified by the barcode scan. The dosage can be verified by looking at the photograph of the syringe, the before and after weights of the vial, the before and after weights of the bag, or any combination of these. Any digital photographs taken during the compounding process may be made available for inspection by the pharmacist. For example, the pharmacist may look at a photograph such as the photograph of FIG. 11 to determine whether excessive bubbles may have been included in the liquid drawn into syringe 206.

Upon completion of the compounding task, pharmacy server 101 may assign another compounding task to compounding station 102a, and download another protocol to compounding assistance device 201 in accordance with the new task.

Figure 14:
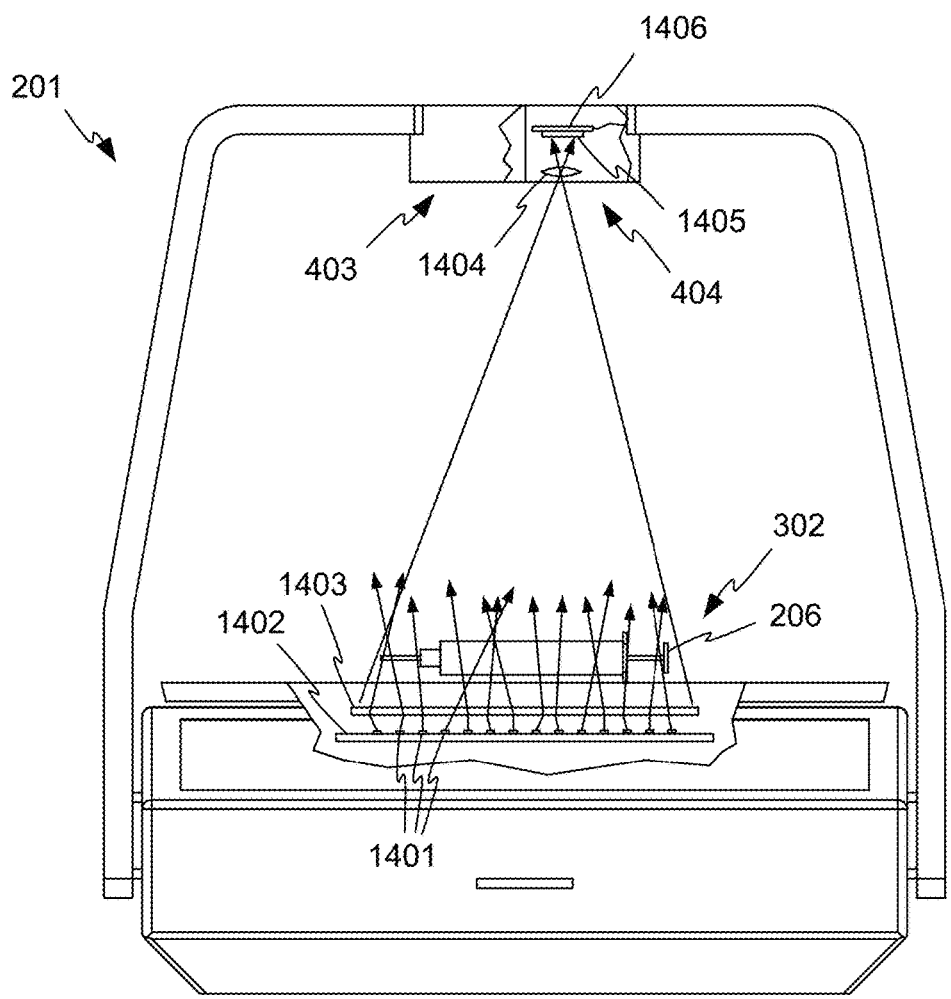
FIG. 14 illustrates the arrangement of an area light source and an infrared camera of the compounding assistance device of FIG. 3, in an embodiment of the invention.

FIG. 14 illustrates the arrangement of area light source 302 and infrared camera 404 of compounding assistance device 201, in an embodiment of the invention.

In this example, area light source 302 includes an array of infrared light emitting diodes (LEDs) 1401 mounted to a circuit board 1402. Light from infrared LEDs 1401 passes through a diffuser 1403, and is scattered upward. Some of the light reaches a lens 1404 of infrared camera 404, which forms an image onto an electronic array light sensor 1405, which in turn is mounted on a printed circuit board 1406. Printed circuit board 1406 may interface with a controller within compounding assistance device 201, to receive signals for controlling electronic array light sensor 1405.

Infrared LEDs 1401 may emit light in the near infrared wavelengths, for example between about 700 and 900 nanometers. In other embodiments, other wavelengths may be used. Diffuser 1403 provides a generally uniform backlight for items placed on area light source 302, for example syringe 206. Area light source 302 may be controlled by an electronic controller within compounding assistance device 201. In some embodiments, tray 209 may be made of a diffusing material, and may be used in addition to or instead of diffuser 1403 to diffuse the light from area light source 302.

In other embodiments, other kinds of light sources may be used, for example an edge-lit light guide plate having scattering features on one side. In this arrangement, light sources direct light into one or more edges of the light guide plate, and the light propagates by total internal reflection within the plate until it strikes one of the scattering features. Some of the scattered light is scattered out of the side of the plate opposite the scattering features. The scattering features are preferably distributed so that the intensity of the light exiting the plate is substantially uniform across the area of the plate. A diffuser may also be used to further diffuse the light exiting the plate, for additional uniformity in brightness.

Electronic array light sensor 1405 may be, for example, a charge coupled device (CCD) sensor, a complementary metal oxide semiconductor (CMOS) sensor, or another suitable kind of sensor. In general, such sensors exploit the property of some semiconductor materials that when the material is struck by light, free electrons are generated in proportion to the intensity of the light. The sensor is divided into specific light-sensitive areas called "pixels". To capture an image, the pixels are reset and then exposed to light for an exposure time. At the end of the exposure time, the amount of charge accumulated in each pixel is measured and converted to a numerical value. An array of these numerical values may be called a "digital image", with each value in the array representing the brightness of the light falling on the corresponding pixel.

In a CCD sensor, the accumulated charges are shifted off of the sensor to a charge amplifier, the output of which is digitized for each pixel. In a CMOS sensor, the accumulated charge can be read from each pixel directly, without shifting.

Electronic array light sensor 1405 may have any number of pixels sufficient to resolve features of interest at tray 209. In some embodiments, electronic array light sensor 1405 may include an array 2560×1920 pixels, or about five megapixels. Other array sizes may be used in other embodiments. Electronic array light sensor 1405 is sensitive to light in the infrared wavelengths emitted by area light source 302. For example, electronic array light sensor 1405 may be a silicon-based sensor sensitive to near infrared light. Infrared camera 404 may include an optical filter (not shown) that excludes other wavelengths. The optical filter may be, for example, a dichroic filter that passes light in the wavelengths of interest, but blocks light in other wavelengths, for example visible light.

As is explained above, infrared camera 404 can produce photographs of items on tray 209 that may be clearer in some aspects relevant to pharmaceutical compounding than photographs taken using visible light camera 403. For example, glare spots caused by ambient room light can be largely eliminated. This clarity facilitates analysis of the digital photographs taken using infrared camera 404 for measurement and annotation that may be helpful to a reviewing pharmacist.

Figure 15:
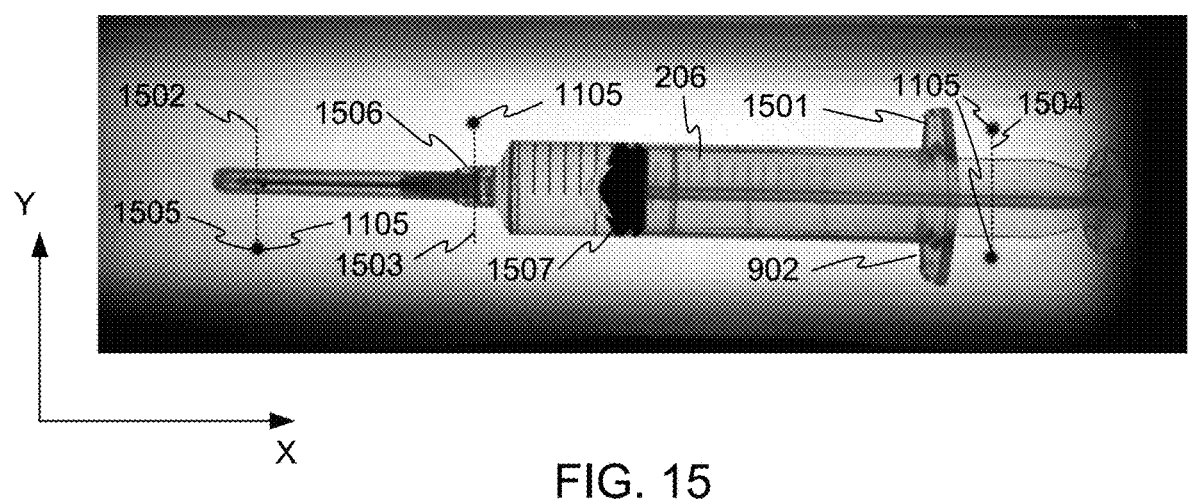
FIG. 15 shows a photograph similar to the photograph of FIG. 11, taken using an infrared camera, and illustrating image analysis in accordance with embodiments of the invention.

FIG. 15 shows a photograph similar to the photograph of FIG. 11, taken using an infrared camera such as infrared camera 404, and illustrating image analysis in accordance with embodiments of the invention. The controller within compounding assistance device 201 may "know" the relative positions of fiducial marks 1105, as measured in image pixels, based on the known locations of fiducial marks 1105 on tray 209, the number of pixels in electronic image sensor 1405, and the magnification of the optical system including lens 1404. The controller can quickly locate the fiducial marks in the image by looking for a pattern of dark spots near the expected locations of the fiducial marks in the image. The pixel locations of the fiducial marks in the image may be recorded for reference.

As is visible in FIG. 15, barrel flange 1501 of syringe 206 has been placed in groove 902 of tray 209, and thus barrel flange 1501 is precisely located with respect to fiducial marks 1105 in the "X" direction shown in FIG. 15. The controller may then query the brightness values of the pixels in the image near the fiducial marks, to locate edges of syringe 206 in the "Y" direction. For example, pixels along column lines 1502, 1503, and 1504 may be analyzed, looking for abrupt light-to-dark and dark-to-light transitions that indicate the presence of edges of parts of syringe 206.

Figure 16:
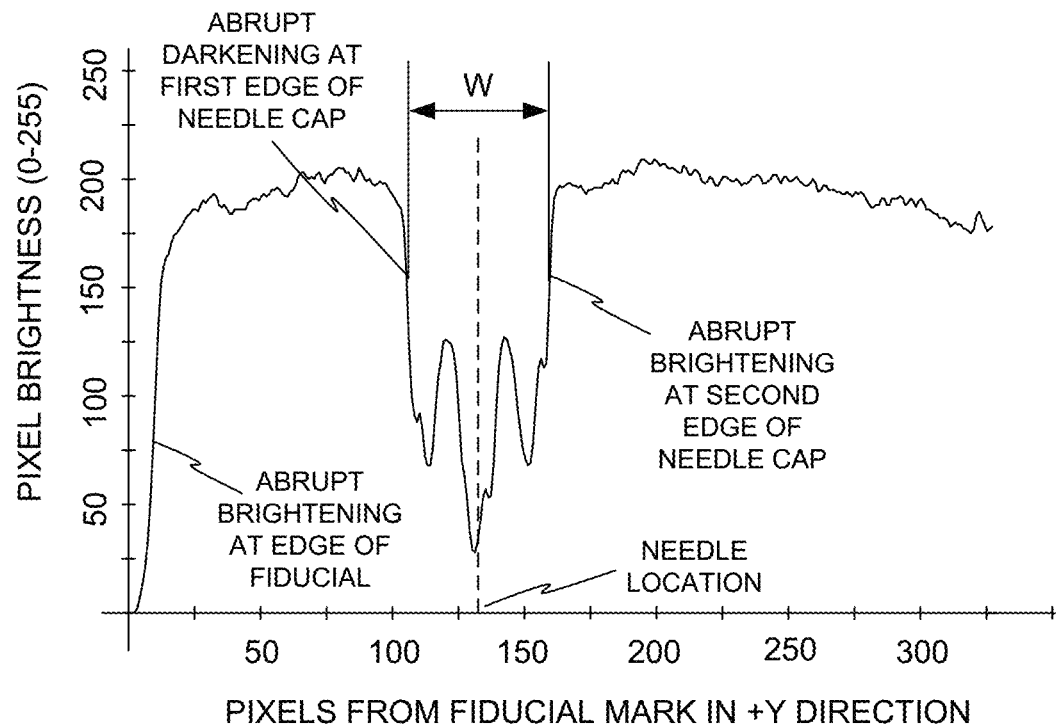
FIG. 16 illustrates an example of a trace of the brightness of pixels along a column line in the image of FIG. 15, in accordance with embodiments of the invention.

FIG. 16 illustrates an example of a trace of the brightness of pixels along column line 1502, moving in the +Y direction from lower left fiducial mark 1505. The transitions spanned by width W may be presumed to include be the needle of syringe 206. If no drop in brightness is detected at the expected location of the needle, then the controller may consider that no needle is attached to syringe 206. Presuming a drop is detected, then the centerline of the region spanned by width W may be presumed to be the centerline of the needle. The width W may be compared with known dimensions of the parts of syringe to determine whether a cap is present on the needle.

Referring again to FIG. 15, similar traces may be performed along other lines to detect the presence and size of a luer lock 1506, or the presence and size of a plunger (not labeled) of syringe 206. The detected dimensions may be compared with stored dimensions of standard syringes, so that the size of syringe 206 is automatically determined.

In other embodiments, other image processing techniques may be used to ascertain the location and size of a syringe from a digital image. For example, a correlation operation may be performed with a previously-prepared syringe photograph. The previous photograph may be compared with the current photograph in a number of orientations and positions, to find the location that best correlates with the syringe in the current photograph, to ascertain the location of the syringe in the current photograph. Fiducial marks 1105 may be found in this way as well. In other embodiments, a synthetic syringe image may be used in the correlation operation. Many other techniques are possible.

Once the size and location of syringe 206 are known in pixel space, the controller may annotate the digital image of the syringe, to assist the pharmacist in reviewing the compounding operation in which the image was taken.

In some embodiments, similar image processing techniques may be used to locate plunger 1507 in the digital image. Given the location of plunger 1507, the location and orientation of syringe 206, and the size of syringe 206, an estimate of the volume of liquid in syringe 206 can be computed.

Figure 17:
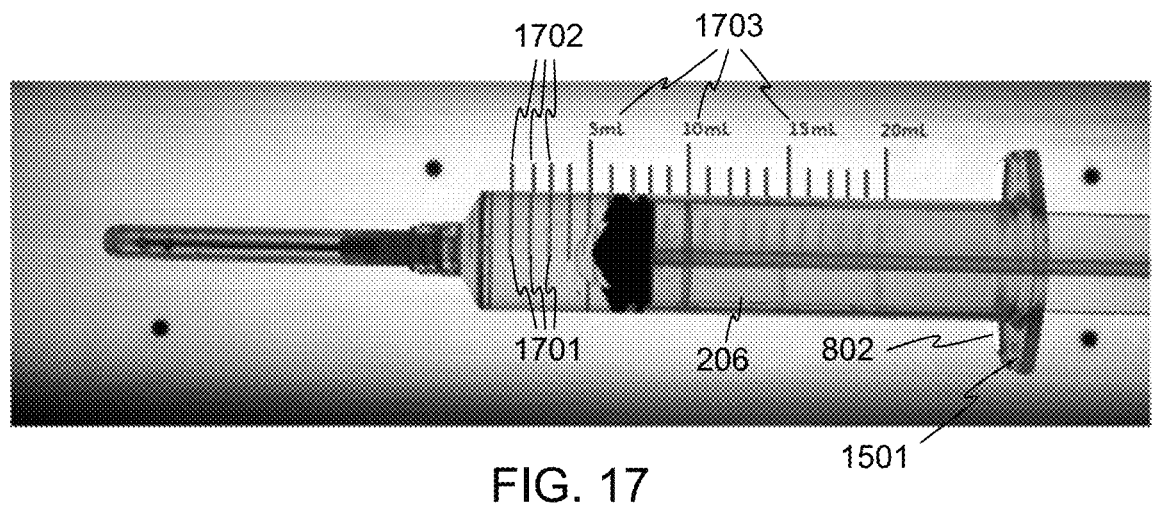
FIG. 17 illustrates a way of annotating an infrared image, in accordance with embodiments of the invention.

FIG. 17 illustrates one way of annotating an infrared image, in accordance with embodiments of the invention. Once the size and location of syringe 206 have been ascertained, the size can be correlated to a standard syringe having pre-recorded measurements, including the locations of gradation marks 1701 on the syringe barrel indicating volumes of liquid in the syringe based on plunger position. While gradation marks 1701 are highly visible in FIG. 17, this may not always be the case. Depending on the positioning of the syringe on tray 209, gradation marks 1701 may not be readily visible in any images. For example, syringe 206 may have been placed on tray 209 with gradation marks 1701 facing downward, or the liquid within syringe 206 may be opaque, hiding gradation marks 1701.

Using the known size and position of syringe 206, compounding assistance device 201 can annotate images taken by either of its cameras to enhance the readability of the plunger position. In FIG. 17, compounding assistance device has altered some of the pixels of the image to show lines 1702 corresponding to the computed locations of gradation marks 1701, and has also added text 1703 showing the liquid volumes represented by lines 1702. In other embodiments, other kinds of annotation may be provided, for example using different colors.

Figure 18:
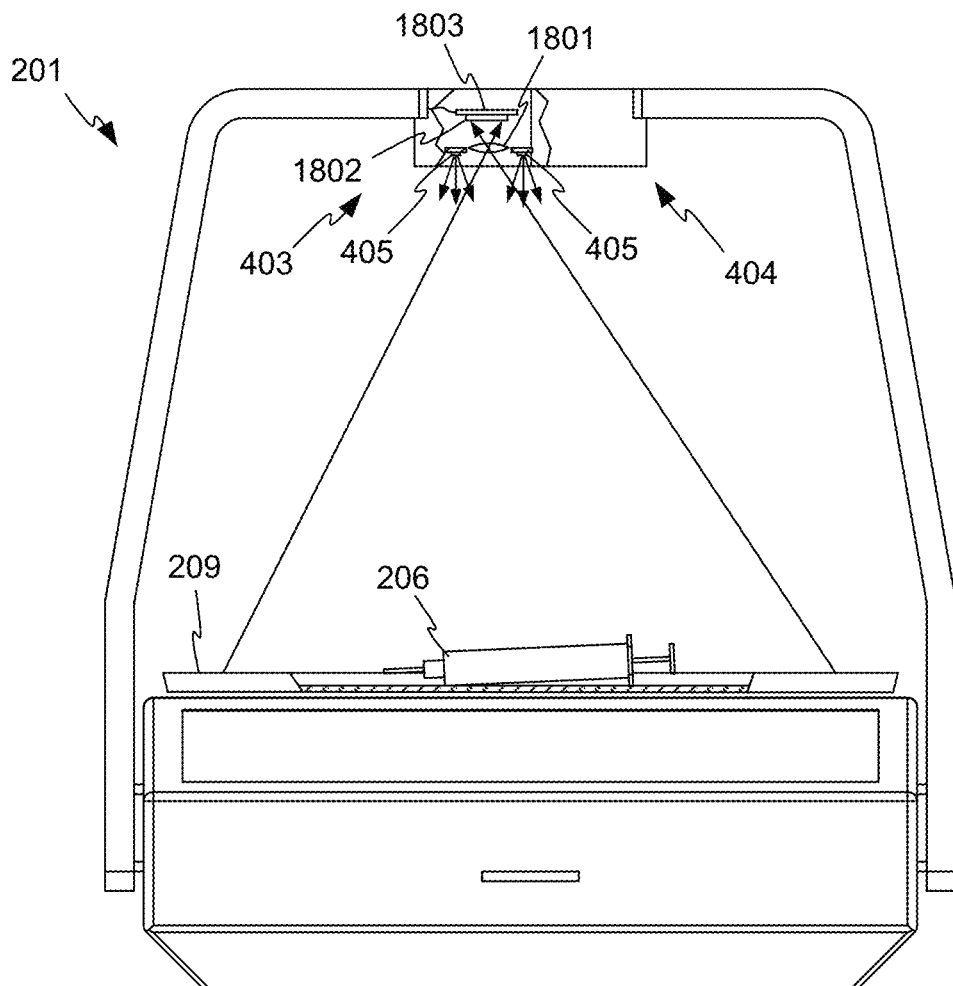
FIG. 18 illustrates the arrangement of a visible light camera in the compounding assistance device of FIG. 3, in an embodiment of the invention.

FIG. 18 illustrates the arrangement of visible light camera 403 of compounding assistance device 201, in an embodiment of the invention. Visible light camera 403 may be used to photograph items on tray 209, for verification that the correct ingredients were used in a compounding task, for final verification that the resulting product looks as it should, or for other purposes. Visible light camera 403 may be a color camera, and may be especially useful for recording the color of a formulation as additional verification that the formulation is likely correct. (Example infrared camera 404 as described above cannot distinguish color due to the narrow band of infrared wavelengths it records and the lack of any color filters on its pixels.)

Visible light camera 403 includes a lens 1801 that focuses light received within its field of view onto an electronic sensor array light sensor 1802, which is in turn mounted on a printed circuit board 1803. Visible light camera 403 may include an optical filter (not shown) such as a dichroic filter that substantially prevents infrared wavelengths from reaching sensor 1802. Light sources 405 may be used to supplement any ambient light illuminating tray 209. For example, light sources 405 may be white LEDs directed at tray 209, and controllable by the controller within compounding assistance device 201.

Electronic array light sensor 1802 may be a CCD sensor, a CMOS sensor, or another suitable kind of sensor as described above, having enough pixels to resolve features of interest at tray 209. For example, sensor 1802 may include an array 2560×1920 pixels, or about five megapixels. Other sensor sizes may be used. Sensor 1802 preferably includes color filters placed over individual pixels so that visible light camera 403 can record color images. For example, sensor 1802 may include red, green, and blue filters in the well-known Bayer pattern.

Visible light camera 403 and infrared camera 404 may be provided as pre-assembled camera modules that include standard interfaces for control by compounding assistance device 201. Suitable camera modules are available from Basler AG of Ahrensburg, Germany, and IDS Imaging Development Systems GmbH of Obersulm, Germany.

Figure 19:
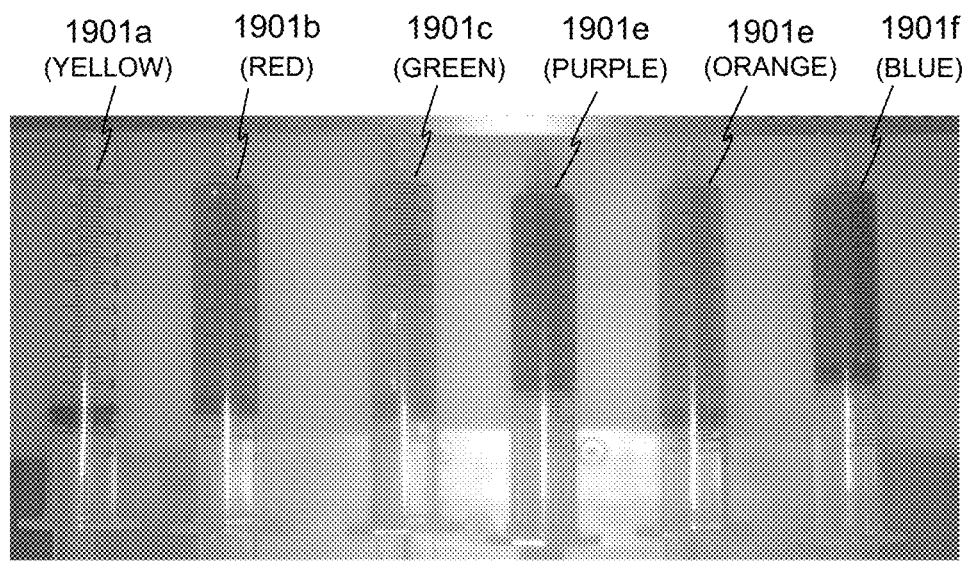
FIG. 19 shows an example photograph of a number of syringes, as may be taken by a visible light camera in accordance with embodiments of the invention.

FIG. 19 shows an example photograph of a number of syringes 1901*a*-1901*f* as may be taken by visible light camera 403 using light sources 405. Each of syringes 1901*a*-1901*f* contains fluid of a different color. Although the fluids in FIG. 19 are not necessarily pharmaceuticals, FIG. 19 illustrates that visible light camera 403 can distinguish a wide range of colors, and a photograph taken with visible light camera 403 may enable a pharmacist to verify that a compounded liquid is of an expected color, bolstering confidence that the compounding was done correctly, or to detect that a compounded liquid is not of the expected color, indicating that the compounding may not have been done correctly.

Figure 20:
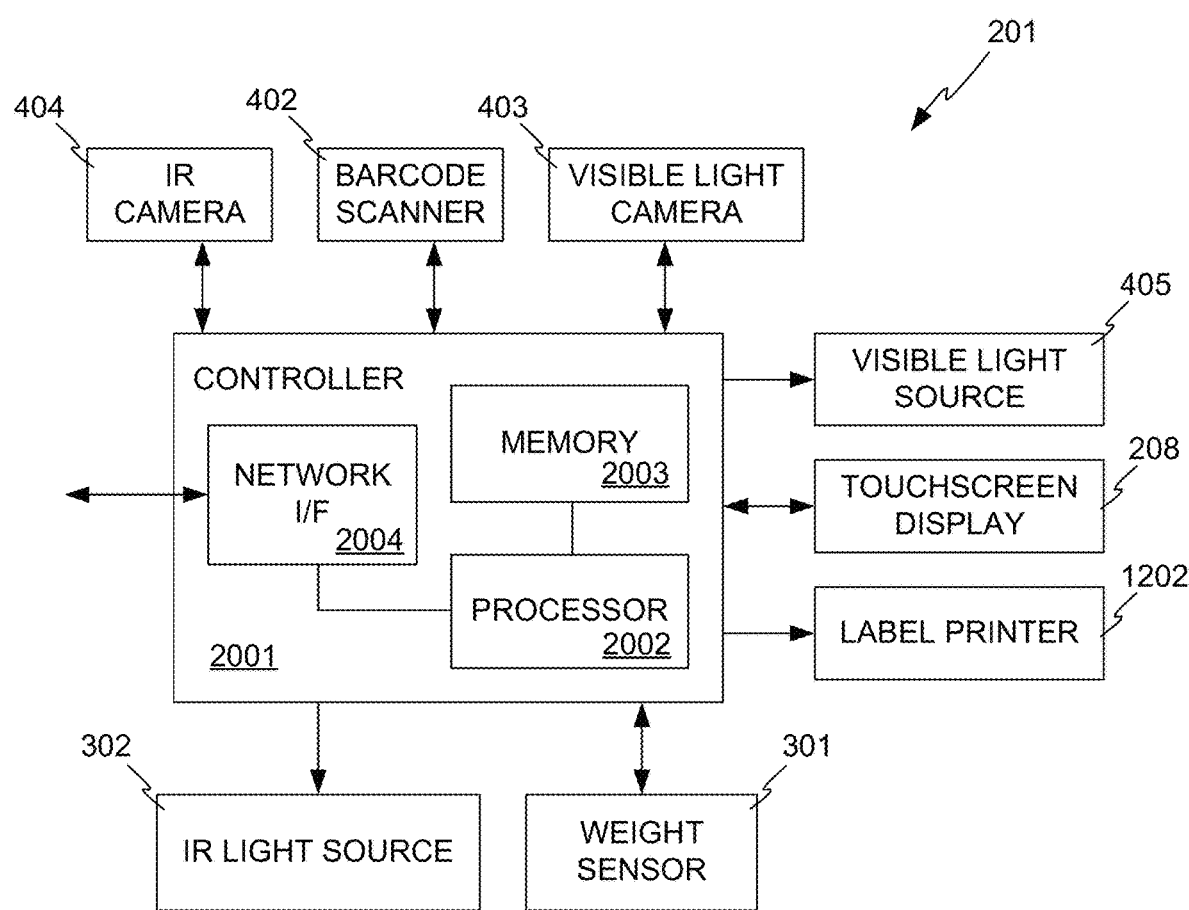
FIG. 20 illustrates a simplified block diagram of the compounding assistance device of FIG. 3, in accordance with embodiments of the invention.

FIG. 20 illustrates a simplified block diagram of compounding assistance device 201, in accordance with embodiments of the invention. Compounding assistance device 201 includes a controller 2001 comprising a processor 2002, memory 2003, and a network interface 2004. Memory 2003 may include dynamic memory, non-volatile memory, mass storage, or other kinds of memory in any suitable combination. Part of memory 2003 holds instructions for processor 2002 that, when executed, control the operation of compounding assistance device 201. Other kinds of information may be stored in memory 2003 as well, for example working copies of digital images, temporary variables, and other kinds of information. Network interface 2004 allows controller 2001 to communication externally, for example with a server such as pharmacy server 101 described above.

Compounding assistance device 201 further includes infrared camera 404, barcode scanner 402, and visible light camera 403 as described above, all in communication with controller 2001 and under the control of controller 2001. Infrared light source 302 and visible light source 405 are also under the control of controller 2001, to be turned on and off at different times. In some embodiments, the intensity of the light produced by either or both light sources may be adjustable under the control of controller 2001. Touchscreen display 208 can communicate information to a user of compounding assistance device 201, and can receive instructions from the user.

Label printer 1303 receives commands and data from controller 2001 for the printing of labels. Weight sensor 301 provides signals to controller 2001 indicating the weight of tray 209 and any items on it.

Other architectures for compounding assistance device 201 may be used.

Additional information about compounding can be found in U.S. patent application Ser. No. 15/827,336 filed Nov. 30, 2017 and titled "IV Compounding Systems and Methods," the entire disclosure of which is hereby incorporated by reference herein for all purposes.

With the above understanding of an example compounding process, it will be recognized that many different compounding tasks are possible, using different numbers and combinations of ingredients. For example, different tasks may be defined for reconstituting and compounding medications received in powdered form, for medications to be delivered in a syringe for direct injection, for diluting medications received in concentrated form, or for other scenarios. More complex workflows may be designed for compounding multiple medications, for example placing multiple medications in a single IV drip bag for simultaneous delivery.

In some embodiments, pharmacy server 101 may oversee a number of pharmacies. For example, a single hospital may include a central pharmacy and one or more satellite pharmacies connected with pharmacy server 101. In other embodiments, pharmacy server 101 may oversee multiple pharmacies in multiple sites. For example, a number of hospitals in a hospital group may share the services of pharmacy server 101.

Figure 21:
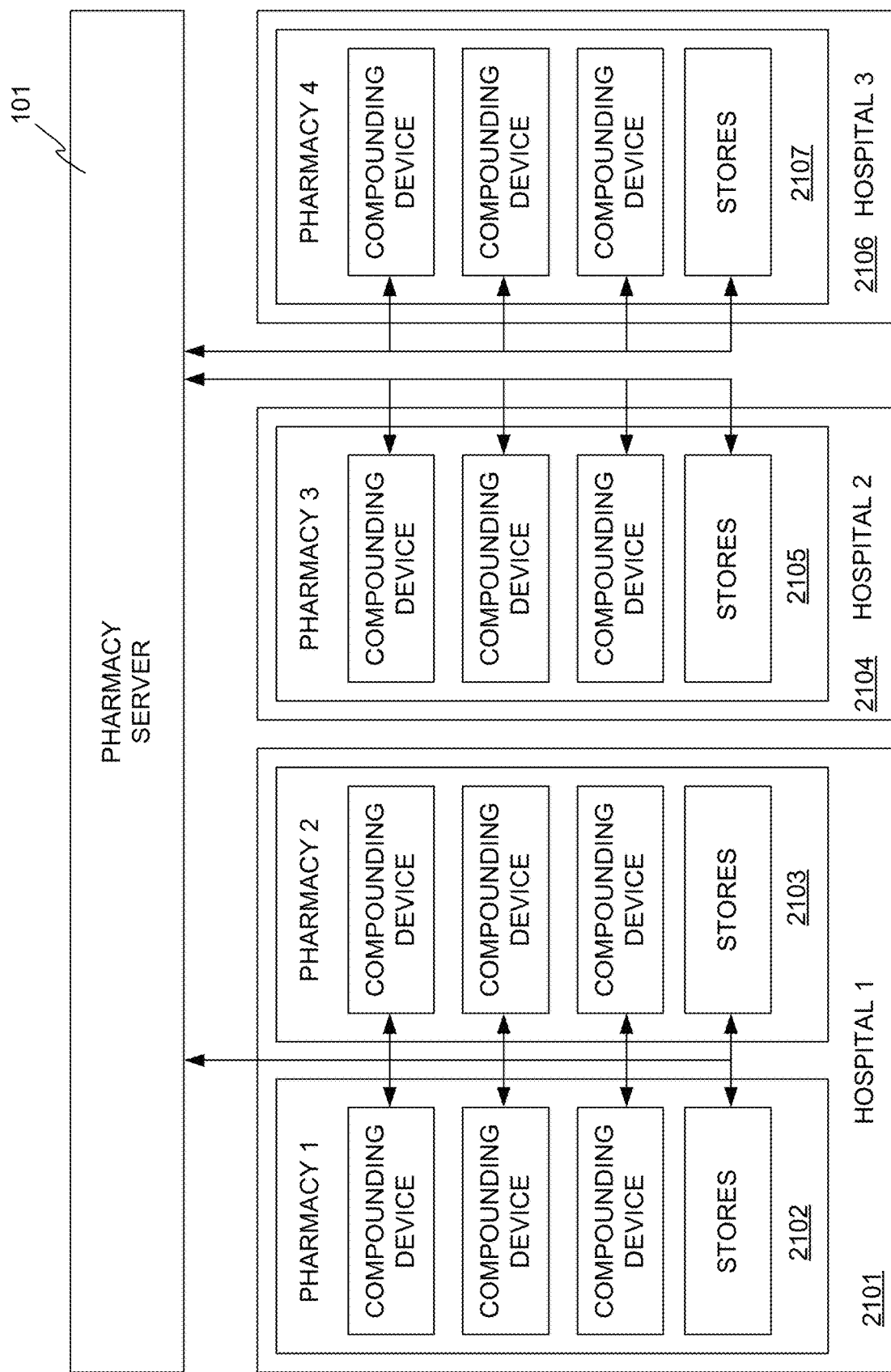
FIG. 21 schematically shows one example arrangement of multiple pharmacies in multiple facilities, all in communication with a pharmacy server, in accordance with embodiments of the invention.

FIG. 21 schematically shows one example arrangement of multiple pharmacies in multiple facilities, all in communication with pharmacy server 101, in accordance with embodiments of the invention. First hospital 2101 includes two pharmacies 2102 and 2103. Second hospital 2104 includes a pharmacy 2105, and third hospital 2106 includes another pharmacy 2107. Each pharmacy houses one or more compounding devices, and stores medicines and supplies. Pharmacy server 101 may be in communication with each of the pharmacies, even to the compounding device level.

Besides the basic requirements of safety and accuracy, the efficient operation of compounding pharmacies in a system such as the system shown in FIG. 21 is the subject of many considerations.

Order Scheduling and Delivery Considerations

Different medication orders may have different priorities. For example, some orders designated as "stat" orders may require immediate compounding for delivery to a patient as soon as possible. Other orders may only need to be filled in due course, but of course should not be subject to unreasonable delay. For example, a "cart fill" order for a set of medications needed for a patient over the next few hours may be filled in due course. In some cases, medications may be prepared in batches, for example "premade" medications. Premade medications may be compounded formulations that are used commonly enough to justify accumulating a supply of them in anticipation of use, rather than compounding them for each individual order. Premades may be prepared in batches during off hours or at other times when compounding capacity is available in one or more of the pharmacies.

Pharmaceutical Beyond Use Considerations

Medications typically have an allowable shelf life, often expressed as a "beyond use" date or time. The beyond use date is a date (or time) after which the medication is not to be used, so as to avoid any risk of loss of effectiveness or other problems with the medication. A single medication may have several beyond use dates or times, depending on its state of use. For example, a vial of medication newly received directly from the manufacturer may have a beyond use date weeks or months or more from the manufacturing date, so long as the vial remains unopened and is stored correctly. Once the vial is opened, it may have a viable shelf life of only hours or days, after which any unused amount should be discarded. And once part of the contents of the vial have been compounded into an IV drip bag, then the bag itself may have a beyond-use date or time measured from the time of compounding. When multiple medications or ingredients are used in a single compounding task, then the beyond use date or time of the compounded formulation may be the ingredient beyond use date or time nearest in the future.

Inventory Management Considerations

Different cooperating pharmacies may have different levels of inventory at different times, which may be located at different physical locations. It may be desirable to cooperatively adjust the management of compounding tasks to efficiently share inventory, while avoiding excessive transportation of items between locations.

Facility Utilization Considerations

The assignment of compounding tasks may be adjusted to allow for different operating times at different satellite pharmacies. Also, different pharmacies may have different equipment, some of which may be more or less suited to certain compounding tasks than equipment at a different pharmacy. All else being equal, certain tasks may be allocated to the pharmacy with the most suited equipment. In another example, different facilities may have different "off" hours than other facilities, when capacity may be available to perform batch compounding to frequently-used formulations.

Compounding Management

In embodiments of the invention, pharmacy server 101 is programmed to assign compounding tasks to the various compounding devices, in light of the above and other considerations, with the goal of efficiently achieving the greatest feasible number of compounding task completions with the least feasible level of resource consumption, all on time and safely. Pharmacy server 101 may be programmed with many rules in pursuit of this goal.

The ability of server 101 to implement its efficiency improvements is enabled in part by the fact that server 101 assigns or "pushes" the compounding tasks to the compounding devices. In at least some prior arrangements, each compounder, upon completion of one compounding task, "pulls" the next available task from a queue. Because the individual compounders do not have visibility to the entire flow of orders or to the status of other pharmacies or facilities, a "pull" system cannot achieve the performance of a system having a global view and implementing a "push" system, as in embodiments of the invention.

For example, when a batch compounding task is planned, server 101 may recognize that two different compounding devices are available to work on the task, but that the two have different historical speeds of performance. In a hypothetical example, compounding workstation 102b may be available, and may historically be able to complete one replication of the task at hand in 5 minutes, when used by the operator on duty. At the same time, robotic compounder 103 may be available, and may be able to complete one replication in 4 minutes. In this example, we suppose that 20 units of the compounded formulation are ordered. Server 101 may allocate the batch preparation to either or both of the two devices, depending on current needs. For example, in order to deliver the entire batch most quickly, server may assign portions of the task to both devices. However, if 10 units are assigned to each device, robotic compounder 103 will complete its 10 units in 40 minutes, while the operator at compounding station 102b will require 50 minutes. Delivery of the entire order will have to wait on compounding station 102b after robotic compounder 103 is finished.

Server 101 may instead assign unequal portions of the task to the two devices. In the above example, server 101 may assign 11 of the units to robotic compounder 103 and only 9 to compounding workstation 102b. Robotic compounder 103 can complete its 11 units in 44 minutes, and the operator at station 102b can complete his or her 9 units in 45 minutes. The overall 20 units are available for delivery in 45 minutes—5 minutes sooner than if equal portions of the task were assigned to the two available devices. Within rounding error, server 101 in this example assigned portions of the task to the two devices such that the two portions were completed at the same time.

A large number of such strategies are possible.

In another example, compounding tasks may be reordered or assigned in groups to minimize the waste of pharmaceuticals. For example, a vial may contain 50,000 units of a pharmaceutical, and two medication orders may arrive at the pharmacy for compounding the pharmaceutical into IV drip bags—one containing 30,000 units of the pharmaceutical and one containing 20,000 units. If these two orders are simply assigned in sequence to the next available compounding devices, each of the devices may use a vial of the pharmaceutical, wasting 20,000 units at one device and 30,000 units at the other. Instead, server 101 may advance one of the others out of turn so that both can be assigned to the same compounding device and filled from the same 50,000 unit vial, resulting in no waste. Even if the two orders were assigned to the same compounding device but separated in time, waste could still occur if the shelf life of the opened vial is exceeded between tasks. The reordering of the tasks to occur in immediate sequence helps avoid this potential for waste as well.

Similarly, if several orders are received for compounding the same medication for different patients, these orders may be grouped and assigned to the same compounding device. In this way, supplies for the multiple orders may be pulled simultaneously and the compounding tasks may be performed without switchover time at the compounding device.

Server 101 may include the scheduled dosage times of the compounded formulations in its assignment rules as well. For example, in the scenario above, the two compounding tasks can also be scheduled so that both compounded IV bags can be delivered to their respective patients during the shelf life of the completed bags. In other words, it can also be important not to complete a compounding task too early, and risk the compounded formulation being unusable by the scheduled time of administration.

In another example, server 101 may assign compounding tasks to particular pharmacies, for example to avoid waste. For example, server 101 may keep or have access to inventory records of multiple pharmacies such as pharmacies 2102, 2103, 2105, and 2107, and may recognize that the stock of a particular pharmaceutical at one of the pharmacies is older than the stock at another of the pharmacies, and may be approaching its beyond use date. Server 101 may receive an order for compounding of the pharmaceutical, and may assign the compounding task to the pharmacy with the oldest viable stock, presuming that the compounded formulation can be delivered to the patient timely. In other embodiments, server 101 may consider the locations of the various pharmacies in this situation. For example, a "stat" order may not be assigned to a pharmacy in a different hospital than the patient for whom it is prescribed, because the time required to transport the compounded formulation back to the patient's hospital may be too long to meet the "stat" requirement. In this case, the order may be assigned for compounding in the same hospital as the patient, even though fulfilling the order in the same hospital may result in waste at another hospital as the same pharmaceutical goes past its beyond use date.

Similarly, server 101 may direct that a pharmaceutical be taken from smaller, more-expensive-per-unit vials than available larger, less-expensive-per-unit vials if the smaller vials are near their beyond-use date and may otherwise be wasted.

In another example, smaller, more-expensive-per-unit vials may be used if there is no convenient stock of the larger, less-expensive-per-unit vials, in order to meet compounding deadlines. In some embodiments, it may be acceptable to substitute an in-stock ingredient for a prescribed out-of-stock ingredient. For example, an IV drip bag with a different diluent than specified in the order may be substituted, preferably with pharmacist and/or physician approval. In some cases, server 101 may keep a list of approved substitutions.

Another management technique is the use of a premade formulation, when available, instead of performing a one-off compounding task. In other situations, a particular pharmacist or physician may specify that a fresh formulation be prepared in a specific case, even though a premade might be available.

Server 101 may consider patient demographics in the assignment of compounding tasks. For example, dose accuracy may be especially critical in pediatric care. When an order is received for a compounded formulation for a young child, a new formulation may be required to be prepared using a protocol with specific checks on the dose accuracy, even though a premade version of the same formulation is in stock, made according to a less stringent protocol and suitable for an adult patient. One way in which this situation may arise is an order for a pediatric dose in which the prescription translates into a dose volume of less than 2 ml. Because the measurement uncertainty of gravimetric verification may be as large as 10 percent or more at such small volumes, a protocol using photographic verification may be specified, showing the syringe plunger position, rather than using gravimetric verification. This decision could also be made based on the specific drug being prescribed. For example, insulin is often prescribed in doses of less than 1 ml, such that photographic verification may be especially appropriate.

In the case of a particularly critical drug or dose size, server 101 may allow the specification of an in-workflow review, in which a second technician is called to review the work of the first and must enter their credentials for the prep to be approved.

In some embodiments, server 101 may consider the time of day, day of the week, day of the month, or other temporal data in assigning compounding tasks. In a simple example, a hospital main pharmacy may operate 24 hours per day, while a satellite pharmacy may close at night. Server 101 may assign a compounding task to the satellite pharmacy closest to the intended patient if the task can be completed during the operating hours of the satellite pharmacy. Otherwise, the task may be assigned to the main pharmacy, even though delivery will require more transportation time and effort. Similarly, tasks may be assigned to pharmacies in different facilities depending on operating hours.

The time of day, week, or month may be considered for other reasons as well. For example, a suburban pharmacy may historically have low demand for compounding on weekday afternoons as compared with a pharmacy in an urban setting. The suburban pharmacy may therefore be available to accept batch compounding tasks during weekday afternoons.

In some embodiments, server 101 may consider the kind of packages in which compounded medications will be delivered in assigning compounding tasks. For example, a series of similar tasks that are suitable for compounding by a robotic compounder may be grouped together and assigned to a particular robotic compounder, while "one-off" compounding tasks may be assigned to workstations with human operators. In some cases, certain delivery packages are simply more amenable to human compounding, for example ampoules, elastomeric pumps, and syringes of unusual size. Compounding tasks involving these delivery vehicles can be assigned to devices with human operators.

Preferably, server 101 can adapt in real time to changing conditions in the pharmacies within its purview. For example, in the event of an equipment breakdown or sudden operator illness, tasks scheduled for assignment to the failed compounding device can be reassigned to other devices.

The above strategies include further examples of the advantage of a "push" assignment system, as opposed to the traditional "pull" system. Pharmacy server 101 has visibility of inventories at the various compounding locations, and can "see" a broader range of incoming medication orders. It can therefor assign compounding tasks in such a way as to maximize the utilization of existing inventories, for example sending orders for the same medication to the same compounding device, so as to fully use a vial, or to use a medication near its beyond use date. A "pull" system in which each device or site has visibility only to its own location would not be able to achieve the same efficiencies.

In another example advantage, server 101 has visibility to the usage of compounding devices at multiple locations, and can assign tasks to take advantage of otherwise-idle devices or to offload devices that would otherwise be overloaded. A pull system would not be able to make these choices.

In another example advantage, the push system can assign portions of a repetitive batch compounding task to different devices, in proportions that maximize the overall speed of completion of the task.

The technical effect of such a system is more efficient utilization of assets and inventory that may be possible with a pull system, through load balancing and efficient inventory usage.

Figure 22:
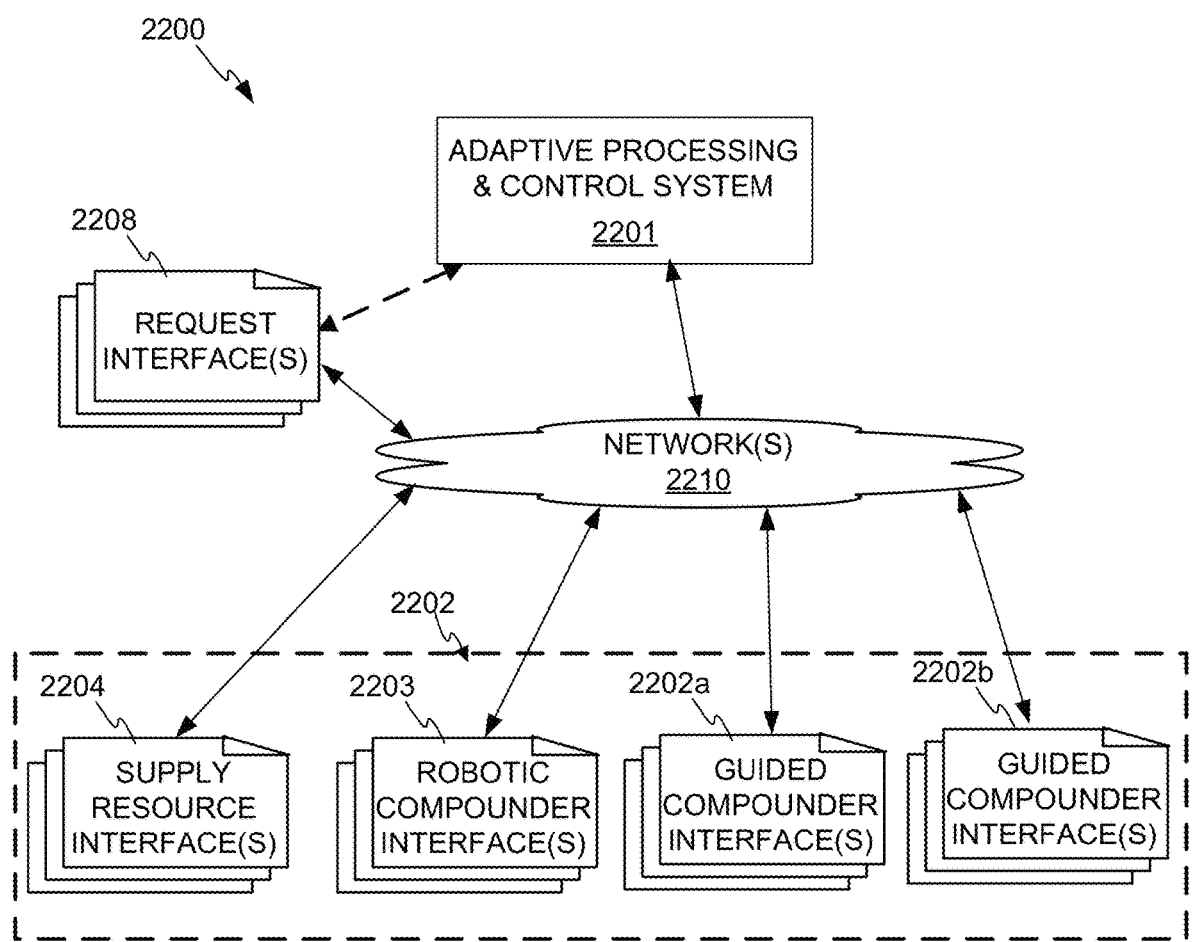
FIG. 22 illustrates a high-level block diagram of a resource control system, in accordance with disclosed embodiments.
Figure 23:
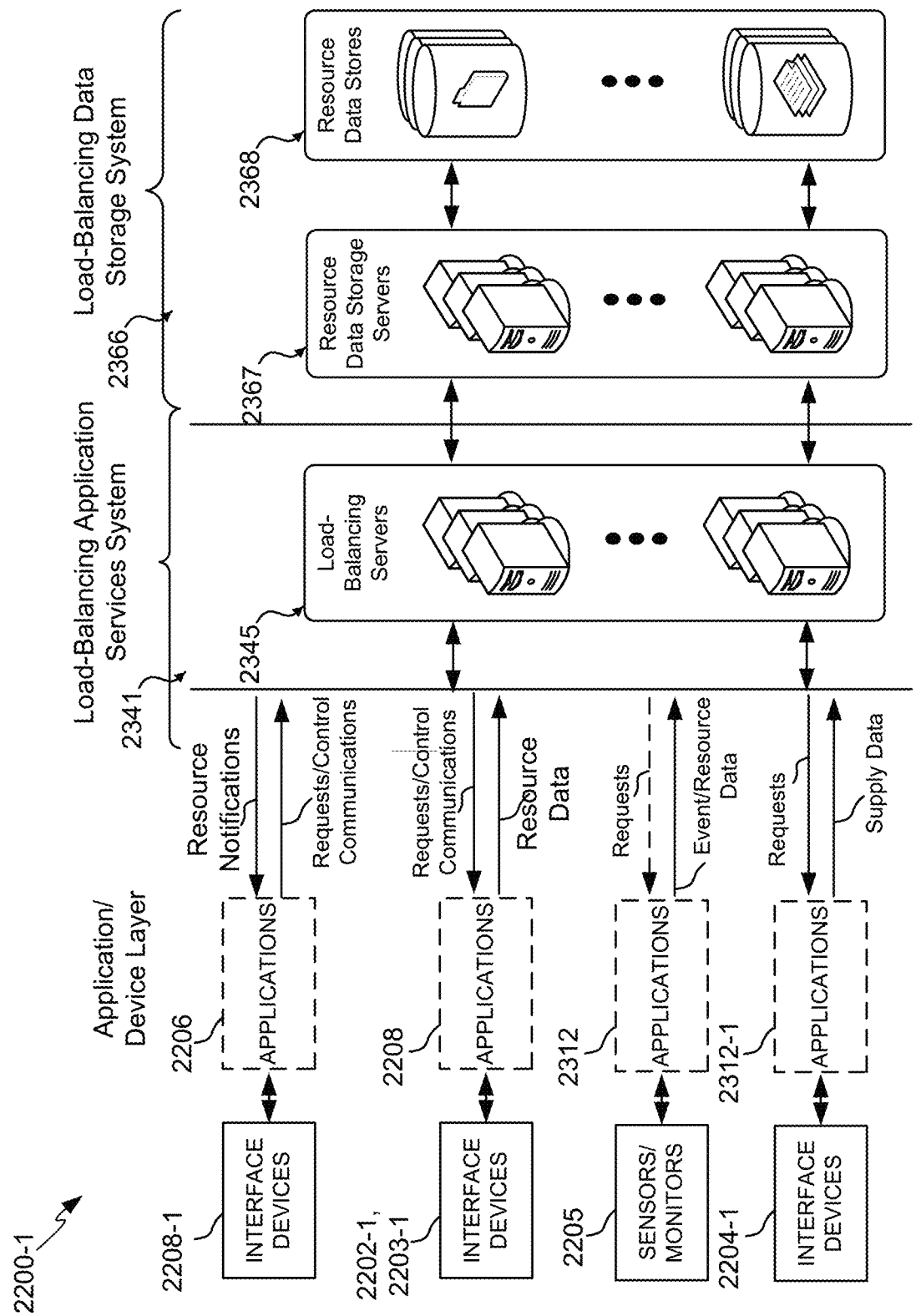
FIG. 23 shows a diagram of a portion of an architecture stack of the system if FIG. 22, in accordance with certain embodiments.

FIGS. 22 and 23 illustrate additional technical details usable in embodiments, implemented as a resource control system 2200. Resource control system 2200 may be used to implement the methods and techniques disclosed herein. FIG. 22 depicts a high-level block diagram of the resource control system 2200, in accordance with disclosed embodiments of the present disclosure. The resource control system 2200 may facilitate resource balancing and notifications relating to resource balancing based at least in part on resource capacities and assignments of operations to resources. In various embodiments, the resource control system 2200 may facilitate resource balancing, notifications, and control relating to resource balancing based at least in part on event recognition, as well. The resource control system 2200 may include an adaptive processing and control system 2201. The adaptive processing and control system 2201 may aggregate and/or determine resource metrics and instantaneous resource state information to dynamically assess resource balance and demand. The adaptive processing and control system 2201 may intelligently manage loads based at least in part on resource models, which may define resources load processing specifications.

In various embodiments, the adaptive processing and control system 2201 may provide resource management control via onsite and/or offsite resource control gateways. As depicted, the resource control system 2200 may allow for interaction between two or more of an adaptive processing and control system 2201, request interfaces 2208, and a plurality of resources interfaces 2202, which may include one or more supply resource interfaces 2204, one or more robotic compounder interfaces 2203, and one or more guided compounder interfaces 2202a, 2202b. As disclosed herein, the one or more robotic compounder interfaces 2203 and one or more guided compounder interfaces 2202a, 2202b may correspond to one or more compounding stations, which may include robotic compounders and guided compounding stations. As depicted, components of the resource control system 2200 may be communicatively coupled or couplable to one or more networks 2210.

The one or more networks 2210 may be a suitable means to facilitate data transfer in the resource control system 2200 and could include multiple networks and/or network components. In various embodiments, the one or more networks 2210 may be implemented with, without limitation, one or more of the Internet, a wide area network (WAN), a local area network (LAN) such as one based on Ethernet, a virtual private network (VPN), an intranet, an extranet, Token-Ring and/or the like, an infra-red network, a wireless network (e.g., a network operating under Bluetooth®, any of the Institute of Electrical and Electronics (IEEE) 802.11 suite of protocols, and/or any other wireless protocol), a wireless local area network (WLAN), a cellular network, such as through 1G, 3G, GSM (Global System for Mobile Communications), etc., another wireless network, a gateway, a public switched telephone network (PSTN), common enterprise network, and/or any other appropriate architecture or system that facilitates the communication of signals, data, and/or message. In various embodiments, the one or more networks 2210 may transmit data using any suitable communication protocol(s), such as, without limitation, TCP/IP (transmission control protocol/Internet protocol), SNA (systems network architecture), IPX (Internet packet exchange), AppleTalk, and/or the like. In various embodiments, the one or more networks 2210 and its various components may be implemented using hardware, software, and communications media such wires, optical fibers, microwaves, radio waves, and other electromagnetic and/or optical carriers; and/or any combination of the foregoing and/or the like. In some embodiments, the network 2210 may include a telephone network that may be circuit switched, package switched, or partially circuit switched and partially package switched.

In various embodiments, the adaptive processing and control system 2201 may include a set of devices configured to process, transform, encode, translate, send, receive, retrieve, detect, generate, compute, organize, categorize, qualify, model, store, display, present, handle, or use information and/or data suitable for the embodiments described herein. The adaptive processing and control system 2201 may include a server system comprising one or more servers, each comprising one or more processors and memory. For example, one or more servers of the system 2201 may be used to store software programs and data. Software implementing the systems and methods described herein may be stored on storage media in the servers. Thus, the software may be run from the storage media in the servers. For example, memory of one or more of the servers may hold instructions that, when executed by one or more processors, cause a load-balancing server to perform its functions in accordance with embodiments of the invention. The storage may also store the records, protocols, and other information collected and generated in the operation of system 2200. For the purposes of this disclosure, the term "memory" encompasses many different kinds of data storage devices and combinations of such devices, for example dynamic memory, static memory, volatile memory, nonvolatile memory, and mass storage such as magnetic or optical disk storage or tape storage. In various embodiments, software implementing the systems and methods described herein may be stored on storage media of other devices described herein.

In some embodiments, the resource control system 2200 may be a distributed system for implementing features of various embodiments disclosed herein. The resource control system 100 may include or otherwise interface with one or more interface devices 2208-1, 2202-1, 2203-1, 2204-1, and/or 2205 depicted in FIG. 22. FIG. 23 shows a diagram of a portion of an architecture stack of the system 2201, in accordance with certain embodiments of the present disclosure. The architecture stack of FIG. 23 may also be used in implementations of the methods and techniques described herein. At least some of the interface devices 2208-1, 2202-1, 2203-1, 2204-1, and/or 2205 may be configured to execute and operate a client application such as a web browser, proprietary client interface, application programming interface, and/or the like over one or more networks 2210. Thus, the system 2201, which may include a server system including one or more servers in some embodiments, may be communicatively coupled with remote interface devices 2208-1, 2202-1, 2203-1, 2204-1, and/or 2205 via the network 2210.

In various embodiments, the adaptive processing and control system 2201 may be adapted to run one or more services or software applications provided by one or more of the components of the system. In some embodiments, these services may be offered as web-based or cloud services or under a Software as a Service (SaaS) model to the users of remote interface devices 2208-1, 2202-1, 2203-1, 2204-1, and/or 2205. Users operating remote interface devices 2208-1, 2202-1, 2203-1, 2204-1, and/or 2205 may in turn utilize one or more client applications to interact with the adaptive processing and control system 2201 to utilize the services provided by these components.

Software components of the resource control system 2200 may be implemented on the adaptive processing and control system 2201—e.g., on one or more servers. In addition or in the alternative, one or more of the components of resource control system 2200 and/or the services provided by these components may be implemented by one or more of the interface devices 2208-1, 2202-1, 2203-1, 2204-1, and/or 2205. Users operating the interface devices 2208-1, 2202-1, 2203-1, 2204-1, and/or 2205 may then utilize one or more client applications to use the services provided by these components. These components may be implemented in hardware, firmware, software, or combinations thereof. It should be appreciated that various different system configurations are possible, which may be different from the resource control system 2200. The embodiment shown in the figure is thus one example for implementing certain embodiments and is not intended to be limiting.

Referring again to FIG. 22, the adaptive processing and control system 2201 may include one or more load-balancing servers, data acquisition servers, application servers, resource data management servers, and/or the like, one or more of which may include one or more load-balancing processors. The server system may be located remotely and/or locally with respect to one or more sites that generate, maintain, supply, and/or otherwise provide resources. The server system may acquire information, manage, and/or control site components of one or more sites, e.g., via resource interfaces 2202. For example, resource descriptions, resource states, resource attributes, and/or the like to push and/or pulled from one or more sites via resource interfaces 2202. Some embodiments may include implementing one or more on-site gateways providing information, management, and/or control of site components.

In various embodiments, one or more of the resource interfaces 2202 may allow for communication with one or more data sources, with the one or more interfaces 2202 configured to operate as one or more event monitors. The server system may correspond to, include, or otherwise utilize one or more event monitors to actively retrieve and/or otherwise receive data from one or more data sources. The one or more data sources may include any suitable source of data to facilitate embodiments disclosed further herein.

In various embodiments, the data from the one or more data sources may be retrieved and/or received by the adaptive processing and control system 2201 via the one or more event monitors through network(s) 2210 and/or through any other suitable means of transferring data. In some embodiments, the adaptive processing and control system 2201 and the data sources could use any suitable means for direct communication. According to certain embodiments, data may be actively gathered and/or pulled from one or more data sources, for example, by accessing a third party repository and/or by "crawling" various repositories. Certain data pulled and/or pushed from the one or more data sources may be transformed and the transformed data and/or other data generated as disclosed herein.

In various embodiments, one or more of the resource interfaces 2202 may include one or more gateways and/or application programming interfaces (APIs) that define protocols and routines for interfacing with the data sources. The APIs may specify application programming interface (API) calls to/from data source systems. Some embodiments may employ one or more web APIs. In some embodiments, the APIs may include a plug-in to integrate with an application of a data source system. The one or more of the resource interfaces 2202, in some embodiments, could use a number of API translation profiles configured to allow interface with the one or more additional applications of the data sources to access data (e.g., a database or other data store) of the data sources. The API translation profiles may translate the protocols and routines of the data source system to integrate at least temporarily with the system and allow communication with the system by way of API calls. Data, as referenced herein, may correspond to any one or combination of raw data, unstructured data, structured data, information, and/or content which may include media content, text, documents, files, instructions, code, executable files, images, video, audio, and/or any other suitable content suitable for embodiments of the present disclosure.

According to certain embodiments, the adaptive processing and control system 2201 may include or provide a resource administratory platform. An administrative device may receive notifications and/or access the adaptive processing and control system 2201 via one or more request interfaces 2208. In some embodiments, resource interfaces 2202 may interface with resource-controlling systems at remote sites.

In some embodiments, one or more request interfaces 2208 and/or a resource interfaces 2202 may include a web interface, which may, for example, allow for real-time and scheduled changing of resource assignments and schedules. The client interfaces 2205 and/or resource data interfaces 2202 may allow for transfer of and access to information in accordance with certain embodiments disclosed herein. In various embodiments, the request interfaces 2208 and/or resource interface(s) 2202 may include one or more suitable input/output modules and/or other system/devices operable to serve as an interface between users and the resource administratory platform. The request interfaces 2208 and/or resource interface(s) 2202 may facilitate communication over the network 2210 using any suitable transmission/communication protocol and/or standard.

In various embodiments, the system 2201 may include, provide, and/or be configured for operation with the request interfaces 2208 and/or resource interface(s) 2202, for example, by making available and/or communicating with one or more of a website, a web page, a web portal, a web application, a mobile application, enterprise software, and/or any suitable application software. In some embodiments, a request interfaces 2208 and/or resource interface(s) 2202 may include an API to interact with the interaction system 2201.

In some embodiments, the request interfaces 2208 and/or resource interface(s) 2202 may include or work with an application made available to one or more interfaces, such as a mobile application as discussed herein. In some embodiments, the request interfaces 2208 and/or resource interface (s) 2202 may cause a web page to be displayed on a browser. The web page(s) may display output and receive input from a user (e.g., by using Web-based forms, via hyperlinks, electronic buttons, etc.). A variety of techniques can be used to create the web pages and/or display/receive information, such as JavaScript, Java applications or applets, JSON, dynamic HTML and/or AJAX technologies. Accordingly, the adaptive processing and control system 2201 may have web site(s)/portal(s) giving access to such information, such as an administratory portal. In various embodiments, a request interfaces 2208 and/or resource interface(s) 102 may include providing one or more display screen images that may each include one or more user interface elements. A user interface may include any text, image, and/or device that can be displayed on a display screen for providing information to a user and/or for receiving user input. A user interface may include one or more widgets, windows, dashboards, text, text boxes, text fields, tables, grids, charts, hyperlinks, buttons, lists, combo boxes, checkboxes, radio buttons, and/or the like.

Referring again to FIG. 23, the depicted portion at least partially includes an application/device layer, as well as a load-balancing application services system 2341 and a load-balancing data management system 2366 of the system 2201. In some embodiments, the load-balancing application services system 2341 may correspond at least partially to an interface layer and a load-balancing application services management layer. In some embodiments, the data storage system may correspond at least partially to a load-balancing data storage layer.

The load-balancing application services system 2341 may interface with the application/device layer 2210 and the load-balancing data storage system 2366. In some embodiments, the load-balancing application services system 2341 may include at least part of the application/device layer 2210. The load-balancing application services system 2341 could be a middle tier of the interaction system 2201 in some embodiments, with the load-balancing data storage system 2366 corresponding to a back-end in some embodiments.

In some embodiments, the load-balancing application services system 2341 and the load-balancing data storage system 2366 each may be or include a load-balancing server system 2345 and a resource data management server system 2367, respectively, that include one or more servers. Other embodiments may include only a single server system. In some embodiments, the load-balancing application services system 2341 and the load-balancing data storage system 2366 may be integrated. In various embodiments, the server systems 2345, 2367 may include one or more computers, specialized server computers (including, by way of example, load-balancing servers, load control servers, other site control servers, data acquisition servers, application servers, data management servers, PC (personal computer) servers, UNIX® servers, mid-range servers, mainframe computers, rack-mounted servers, etc.), server farms, server clusters, or any other appropriate arrangement and/or combination. In various embodiments, the server systems 2345, 2367 may be adapted to run one or more services, operations, processing, or software applications described herein. The server systems 2345, 2367 may also run any of a variety of additional server applications and/or mid-tier applications, including the examples disclosed above, for example, with respect to server 2312.

In some embodiments, the server systems 2345, 2367 may include one or more applications to pull, receive, analyze, aggregate, and/or consolidate data feeds and/or event updates received from various data sources. As an example, data feeds and/or event updates may include, but are not limited to, application 2206, 2208, 2312, and/or 2312-1 updates and/or data feeds, interfaces/devices updates and/or data feeds corresponding to the depicted feedback communications, which may include real-time events and/or data feeds related to sensor systems and/or components thereof, updates (real-time and/or otherwise) received from one or more third party information sources and/or continuous data streams, and/or the like. The server system 2345 may also include one or more applications to display the data feeds and/or real-time events via the interfaces/devices and/or devices internal to the adaptive processing and control system 2201.

The application services system 2341 and/or the data management system 2366 may also include one or more resource data storages 2368. The resource data storages 2368 may include various forms of data storage including solid state storage, disk storage, databases (including relational, column, document, key-value and graph type databases) and cache. The resource data storages 2368 may reside in a variety of locations, such as on a non-transitory storage medium local to (and/or resident in) the server systems 2345, 2367 and/or remote from the server systems 2345, 2367 and in communication with the server systems 2345, 2367 via a network-based or dedicated connection. In certain embodiments, the resource data storages 2368 may reside in a storage-area network (SAN). Similarly, any necessary files for performing the functions attributed to the server systems 2345, 2367 may be stored locally on the server systems 2345, 2367 and/or remotely, as appropriate. In one set of embodiments, the resource data storages 2368 may include relational databases that are adapted to store, update, and retrieve data in response to SQL-formatted commands. It should be appreciated that information corresponding to the repositories may be stored elsewhere and/or in other ways, or may not be stored, depending on the implementations chosen. Likewise, while various segregations of data corresponding to the repositories are provided herein, it should be appreciated that such examples are non-limiting, and some or all the data may be handled in any suitable manner.

In certain embodiments, the adaptive system 2201 may be implemented in or with a distributed computing and/or cloud computing environment with a plurality of servers and cloud-implemented processing, memory, and data resources. Thus, with accretion of service information, the system may allow for scaling out with additional processing resources, server resources, data storage resources, data management resources, and the like. Some embodiments may use different types of servers to service different types of interface devices. The adaptive system 2201 may provision services facilitated by one or more components of the adaptive system 2201, and, in some embodiments, one or more of the services may be offered as cloud services. A specific instantiation of a service provided by the adaptive system 2201 may be referred to herein as a service instance. In some examples, a service provided by the adaptive system 2201 may include control communications, which may correspond to any one or combination of communications disclosed herein such as communications to effect resource assignment, resource assignment such as assignment nullification, modification, reassignment, etc.

In the illustrated embodiment, one or more interface devices may be used by users to interact with the adaptive system 2201. Although only a limited number of the interface devices is shown, any number of interface devices may be supported. In various embodiments, the interface devices may correspond to the request interfaces 2208 and/or resource interfaces 2202. In various embodiments, the interface devices may include site component controllers and/or site components as disclosed further herein.

According to a first embodiment, a system for compounding of medications comprises a plurality of compounding devices, each of the plurality of compounding devices selected from the group of compounding devices consisting of a compounding assistance device, a robotic compounder, and a hazardous drug robotic compounder, and each of the plurality of compounding devices being computerized. The system further comprises a central server computer, and each of the plurality of compounding devices is in bidirectional communication with the central server computer via an electronic network. The central server computer and the plurality of compounding devices are configured to cooperatively receive, at the central server computer, a plurality of requests, at least some of which require the compounding of one or more medications; push, by the central server computer via the electronic network, assignments of respective compounding tasks to the plurality of compounding devices; and perform or guide, using the compounding devices, the respective directed compounding operations. The central server computer is configured to assign respective compounding tasks to the plurality of compounding devices in accordance with a set of rules designed to promote efficient use of compounding resources and avoid waste.

According to a second embodiment, the plurality of compounding devices in the first embodiment reside within a single pharmacy.

According to a third embodiment, the plurality of compounding devices in the first embodiment are distributed among multiple pharmacies within a single facility.

According to a fourth embodiment, the plurality of compounding devices in the first embodiment are distributed among multiple facilities.

According to a fifth embodiment, the central server computer in any of the above embodiments is configured to assign respective compounding tasks to the plurality of compounding devices in accordance with a rule that considers the physical locations of the plurality of compounding devices.

According to a sixth embodiment, the set of rules in any of the above embodiments is configurable.

According to a seventh embodiment, the set of rules in any of the above embodiments comprises one or more rules for reordering or grouping requests so as to avoid waste.

According to an eighth embodiment, the central server computer in any of the above embodiments is configured to assign respective portions of a batch compounding task to at least two of the plurality of compounding devices, wherein the respective portions of the batch compounding task assigned to each of the at least two compounding devices are selected based at least on part on performance records of the at least two compounding devices, such that the portions of the batch compounding task assigned to the at least two compounding devices are expected to be completed at the same time.

According to a ninth embodiment, compounding tasks are assigned in any of the above embodiments based at least in part on a beyond use date or time of a particular pharmaceutical.

According to a tenth embodiment, compounding tasks in any of the above embodiments are assigned based at least in part on one or more of a time of day, day of the week, or day of the month at which a particular compounding task is to be performed.

According to a eleventh embodiment, at least one batch compounding task is assigned in any of the above embodiments in a way that utilizes a compounding device for preparation of a batch of compounded formulation when the compounding device would otherwise be idle.

According to a twelfth embodiment, compounding tasks are assigned in any of the above embodiments based at least in part on patient demographics.

According to a thirteenth embodiment, at least some compounding tasks involving the same pharmaceutical are grouped and assigned in any of the above embodiments to be performed on a single compounding device.

According to a fourteenth embodiment, the central server computer is configured in any of the above embodiments to maintain records of the performance of each of the plurality of compounding devices, and compounding tasks are assigned to the compounding devices based at least in part on the records.

According to a fifteenth embodiment, the plurality of compounding devices in any of the above embodiments includes at least one compounding assistance device comprising: a carrier for supporting items, wherein the material of the carrier is not opaque to infrared light; an infrared digital camera positioned to photograph at least a portion of the carrier from above; an area light source positioned under the carrier, the area light source configured to generate infrared light and direct the infrared light through the carrier and toward the digital camera; a display; a weight sensor on which the carrier rests, the weight sensor configured to produce a signal indicating the weight of the carrier and any items on the carrier; a visible light camera positioned to photograph at least a portion of the carrier from above; and a controller configured to guide a user of the compounding assistance device through a pharmaceutical compounding task using one or more prompts shown on the display.

According to a sixteenth embodiment, a method of load balancing in a compounding system comprises receiving, at a central server computer, a plurality of requests, at least some of which require the compounding of one or more medications. The method further comprises monitoring the availability and performance of a plurality of compounding devices, each of the plurality of compounding devices selected from the group of compounding devices consisting of a compounding assistance device, a robotic compounder, and a hazardous drug robotic compounder, and each of the plurality of compounding devices being computerized. The method further comprises, for each of the requests requiring compounding: selecting one of the plurality of compounding devices to which to assign the task of compounding the medication, the selection being performed in accordance with a set of rules designed to promote efficient use of compounding resources and avoid waste; transmitting an electronic message assigning the task of compounding the medication to the selected compounding device; and performing or guiding, using the selected compounding device, the assigned compounding task.

According to a seventeenth embodiment, the plurality of compounding devices in the sixteenth embodiment all reside in a single facility.

According to an eighteenth embodiment, the plurality of compounding devices in the sixteenth embodiment are distributed among multiple facilities.

According to a nineteenth embodiment, for at least a particular one of the requests in any of the sixteenth to eighteenth embodiments, the selected compounding device is a robotic compounder, and the method comprises, performing the assigned compounding task using the robotic compounder.

According to a twentieth embodiment, the method of any of the sixteenth to nineteenth embodiments further comprises tracking inventory levels of medicines at one or more locations, and selecting one of the plurality of compounding devices to which to assign a particular task comprises selecting the compounding device based at least in part on the inventory levels.

According to a twenty-first embodiment, the plurality of compounding devices in any of the seventeenth to twentieth embodiments are distributed among multiple facilities.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. It is to be understood that any workable combination of the elements and features disclosed herein is also considered to be disclosed.

The invention has now been described in detail for the purposes of clarity and understanding. However, those skilled in the art will appreciate that certain changes and modifications may be practiced within the scope of the appended claims.

What is claimed is:

1. A pharmaceutical compounding device, comprising:
   an infrared area light source;
   an infrared digital camera;
   a visible light digital camera;
   a source of visible light positioned adjacent the visible light digital camera;
   a viewing area between the infrared area light source and the infrared digital camera; and
   a controller programmed to control the infrared area light source and the infrared digital camera to take a first photograph of an item in the viewing area such that the item is backlit by the infrared area light source, and to take a second photograph of the viewing area using the visible light digital camera, and to control the source of visible light.

2. The pharmaceutical compounding device of claim 1, wherein:
   the pharmaceutical compounding device is a compounding assistance device comprising a display; and
   the controller is further programmed to guide a user of the device through a compounding task using prompts shown on the display.

3. The pharmaceutical compounding device of claim 1, wherein the pharmaceutical compounding device is a compounding robot.

4. The pharmaceutical compounding device of claim 1, wherein the second photograph comprises a color photograph.

5. The pharmaceutical compounding device of claim 1, wherein the second photograph is associated with the first photograph.

6. The pharmaceutical compounding device of claim 1, wherein the controller is further programmed to automatically analyze at least one of the first photograph or the second photograph.

7. The pharmaceutical compounding device of claim 6, wherein the controller is programmed to automatically analyze at least one of the first photograph or the second photograph to determine a volume of liquid in a syringe received in the viewing area.

8. The pharmaceutical compounding device of claim 6, wherein the controller is programmed to automatically analyze at least one of the first photograph or the second photograph to ascertain a size and position of a syringe received in the viewing area in the at least one of the first photograph or the second photograph.

9. The pharmaceutical compounding device of claim 8, wherein automatically analyzing the at least one of the first photograph or the second photograph to ascertain the size and position of a syringe received in the viewing area in the at least one of the first photograph or the second photograph comprises comparing previous photographs of syringes to the at least one of the first photograph or the second photograph.

10. The pharmaceutical compounding device of claim 8, wherein automatically analyzing the at least one of the first photograph or the second photograph to ascertain the size and position of a syringe received in the viewing area in the at least one of the first photograph or the second photograph comprises comparing a synthetic syringe image to the at least one of the first photograph or the second photograph.

11. The pharmaceutical compounding device of claim 6, wherein the controller is programmed to automatically analyze at least one of the first photograph or the second photograph to ascertain whether a needle is attached to a syringe received in the viewing area.

12. The pharmaceutical compounding device of claim 11, wherein automatically analyzing the at least one of the first photograph and the second photograph to ascertain whether the needle is attached to the syringe comprises:
   identifying an expected location of the needle; and
   evaluating pixel brightness at the expected location of the needle.

13. The pharmaceutical compounding device of claim 12, wherein evaluating pixel brightness at the expected location of the needle comprises:
   identifying a column line; and
   evaluating pixel brightness along the column line.

14. The pharmaceutical compounding device of claim 13, wherein evaluating pixel brightness along the column line comprises identifying abrupt light-to-dark and dark-to-light transitions.

15. The pharmaceutical compounding device of claim 13, wherein automatically analyzing the at least one of the first photograph or the second photograph to ascertain a size and position of the syringe in the at least one of the first photograph or the second photograph comprises:
   identifying a column line extending across the syringe; and
   evaluating pixel brightness along the column line.

16. The pharmaceutical compounding device of claim 15, wherein evaluating pixel brightness along the column line comprises identifying abrupt light-to-dark and dark-to-light transitions.

17. The pharmaceutical compounding device of claim 15, wherein evaluating pixel brightness along the column line comprises identifying a size of a plunger of the syringe.

18. The pharmaceutical compounding device of claim 17, wherein automatically analyzing the at least one of the first photograph or the second photograph to ascertain the size and position of the syringe in the at least one of the first photograph or the second photograph further comprises comparing the size of the plunger of the syringe to stored dimensions of standard syringes.

\* \* \* \* \*